United States Patent
Högberg et al.

(10) Patent No.: US 11,590,130 B2
(45) Date of Patent: Feb. 28, 2023

(54) COMBINATIONS OF A TUBULIN POLYMERIZATION INHIBITOR AND A POLY (ADP-RIBOSE) POLYMERASE (PARP) INHIBITOR FOR USE IN THE TREATMENT OF CANCER

(71) Applicant: NOVIGA RESEARCH AB, Tullinge (SE)

(72) Inventors: Marita Högberg, Tullinge (SE); Stefan Rehnmark, Tullinge (SE)

(73) Assignee: NOVIGA RESEARCH AB, Tullinge (SE)

( * ) Notice: Subject to any disclaimer, the term of this patent is extended or adjusted under 35 U.S.C. 154(b) by 31 days.

(21) Appl. No.: 16/981,232

(22) PCT Filed: Apr. 4, 2019

(86) PCT No.: PCT/SE2019/050312
§ 371 (c)(1),
(2) Date: Sep. 15, 2020

(87) PCT Pub. No.: WO2019/194738
PCT Pub. Date: Oct. 10, 2019

(65) Prior Publication Data
US 2021/0052583 A1    Feb. 25, 2021

(30) Foreign Application Priority Data

Apr. 5, 2018 (SE) .................................. 1850380-5

(51) Int. Cl.

| | |
|---|---|
| *A61K 31/502* | (2006.01) |
| *A61P 35/04* | (2006.01) |
| *A61K 31/496* | (2006.01) |
| *A61K 31/506* | (2006.01) |
| A61K 45/06 | (2006.01) |

(52) U.S. Cl.
CPC .......... *A61K 31/502* (2013.01); *A61K 31/496* (2013.01); *A61K 31/506* (2013.01); *A61P 35/04* (2018.01); A61K 45/06 (2013.01)

(58) Field of Classification Search
CPC .. A61K 31/502; A61K 31/496; A61K 31/506; A61P 35/04
See application file for complete search history.

(56) References Cited

U.S. PATENT DOCUMENTS

| | | |
|---|---|---|
| 9,132,120 B1 | 9/2015 | Tomkinson et al. |
| 2009/0123419 A1 | 5/2009 | Sherman et al. |
| 2009/0149397 A1 | 6/2009 | Ossovskaya et al. |
| 2017/0209594 A1 | 7/2017 | Goldenberg et al. |

FOREIGN PATENT DOCUMENTS

| | | |
|---|---|---|
| WO | WO 2007/084532 A2 | 7/2007 |
| WO | WO 2008/146035 A1 | 12/2008 |
| WO | WO 2009/118384 A1 | 10/2009 |
| WO | WO 2010/091140 A1 | 8/2010 |
| WO | WO 2011/151423 A1 | 12/2011 |
| WO | WO 2012/127032 A1 | 9/2012 |
| WO | WO 2014/168991 A1 | 10/2014 |
| WO | WO 2017/013593 A1 | 1/2017 |
| WO | WO 2017/083979 A1 | 5/2017 |
| WO | WO 2017/223516 A1 | 12/2017 |

OTHER PUBLICATIONS

Liu et al., "Targeting BRCA1/2 deficient ovarian cancer with CNDAC-based drug combinations", Cancer Chemotherapy and Pharmacology, 2018, 81: 255-267.
Mita et al., "Phase 1 First-in-Human Trial of the Vascular Disrupting Agent Plinabulin (NPI-2358) in Patients with Solid Tumors or Lymphomas", Clinical Cancer Research, 2010, 16(23): 5892-5899.
Vanderstichele et al., "Antiangiogenic therapies in ovarian cancer", MEMO—Magazine of European Medical Oncology, Feb. 23, 2018, 11: 18-26.
Yuan et al., "PARP inhibitors as antitumor agents: a patent update (2013-2015)", Expert Opinion on Therapeutic Patents, 2016, 27(3): 363-382.

*Primary Examiner* — Shobha Kantamneni
(74) *Attorney, Agent, or Firm* — James S. Keddie; Bozicevic, Field & Francis LLP

(57) ABSTRACT

Methods and combination therapies for treating, preventing, and/or delaying the onset and/or development of cancer using a tubulin polymerization inhibitor such as a compound of formula I, or a pharmaceutically acceptable salt thereof, and a poly (ADP-ribose) polymerase (PARP) inhibitor, or a pharmaceutically acceptable salt thereof, are provided.

11 Claims, 2 Drawing Sheets

COMBINATIONS OF A TUBULIN POLYMERIZATION INHIBITOR AND A POLY (ADP-RIBOSE) POLYMERASE (PARP) INHIBITOR FOR USE IN THE TREATMENT OF CANCER

CROSS-REFERENCE TO RELATED APPLICATIONS

This application is a § 371 national phase of International Application No. PCT/SE2019/050312, filed on Apr. 4, 2019, which claims the benefit of Swedish Application No. 1850380-5, filed on Apr. 5, 2018, which application is incorporated by reference herein.

FIELD OF THE INVENTION

Methods and combination therapies for treating, preventing, and/or delaying the onset and/or development of cancer using a compound of formula I or a pharmaceutically acceptable salt thereof, and a poly (ADP-ribose) polymerase (PARP) inhibitor, or a pharmaceutically acceptable salt thereof, are provided.

BACKGROUND OF THE INVENTION

Cancer is a phrase used describing a wide variety of diseases that are each characterized by the uncontrolled growth of a particular type of cell. It begins in a tissue containing such a cell and, if the cancer has not spread to any additional tissues at the time of diagnosis, may be treated by, for example, surgery, radiation, or another type of localized therapy. However, when there is evidence that cancer has metastasized from its tissue of origin, different approaches to treatment are typically used. Indeed, because it is not possible to determine with certainty the extent of metastasis, systemic approaches to therapy are usually undertaken when any evidence of spread is detected. These approaches involve the administration of, for example, chemotherapeutic drugs that interfere with the growth of rapidly dividing cells, such as cancer cells. Other approaches involve the use of immunotherapy, in which an immune response against cancerous cells in a subject is elicited or enhanced.

Ovarian cancer (OC) is caused by uncontrollable cell growth in the ovarian tissue and epithelial OC accounts for 90% of all OCs. OC is the seventh most common cancer in women worldwide, with nearly a quarter of a million women diagnosed with it each year. Responsible for approximately 140,000 deaths per annum, this cancer has the highest mortality rate of all gynaecological cancers. Staggering statistics show that only 45% of women with OC are likely to survive for five years compared to up to 89% of women with breast cancer. One of the biggest challenges facing ovarian cancer treatment is the late stage (III and IV) diagnosis due to nonspecific symptoms and lack of simple, routine tests for screening of the disease. It is reported that approximately 75% of patients present with stage III or IV disease at the time of diagnosis (Jelovac D, Armstrong D K. Recent Progress in the Diagnosis and Treatment of Ovarian Cancer. *CA: a cancer journal for clinicians*. 2011; 61(3): 183-203. doi:10.3322/caac. 20113).

Current treatment strategies for OC involve surgery and platinum-based chemotherapy, usually the tubulin inhibitor drug paclitaxel and the anti-neoplastic agent carboplatin are used as the gold standard. Although 70% to 80% of late stage OC patients initially respond well to this therapy combination, more than 60% of these patients will suffer a recurrence of disease (termed refractory OC) due to multidrug resistance and it will be fatal in 70% to 90% (Mantia-Smaldone G M et al., Targeted treatment of recurrent platinum-resistant ovarian cancer: current and emerging therapies. *Cancer Management and Research*. 2011; 3:25-38).

OC is a silent disease that usually is diagnosed at a late stage, and around 75% of the patients are diagnosed at an advanced-stage (stage III and IV). The combination of carboplatin and paclitaxel given every 3 weeks remains the standard first line chemotherapy for OC. However, resistance to the first line chemotherapy is common in patients with advanced disease and around 80% of the patients with stage III or IV disease will relapse after first line combination chemotherapy. There is considerable heterogeneity with regard to overall drug sensitivity, but patients with recurrent OC eventually develop platinum- and/or platinum/paclitaxel—resistant disease. Current second line therapy to resistant/refractory OC is dependent on resistance mechanisms and different combinations of different cytotoxic agents, targeted agents and anti-angiogenesis biologic drugs are being used with limited therapeutic efficacy. The relative 5 years survival is poor, especially for women diagnosed with advanced disease.

Microtubules are important components of the cytoskeleton of eukaryotic cells and have an important role in various cellular functions, such as cell signaling and mitosis. It is a validated drug target in oncology and there are approved anti-cancer drugs on the market targeting microtubules (e.g. paclitaxel, vincristine, sagopilone). Tubulin targeting compounds are characterized by their binding to tubulin and their effects on tubulin polymerization. The compounds exhibit their anticancer properties by interfering with the dynamics of tubulin resulting in mitotic arrest. There are two classes of tubulin targeting compounds: i) inhibitors of tubulin depolymerization (e.g. paclitaxel, docetaxel, sagopilone) and ii) inhibitors of tubulin polymerization (e.g. colchicine, combretastatin, vincristine and vinblastine). The tubulin-binding site has been described for its ability to bind a naturally occurring tricyclic alkaloid colchicine, which inhibits tubulin polymerization. Colchicine itself is not a useful anticancer agent because of its narrow therapeutic window, but compounds with diverse chemical structures that bind to this site or near are now in clinical or preclinical developments e.g. combretastatin CA-4P (zybrestat), AVE-8062 (ombrabulin), BNC105P, MPC-6827 (azixa), ZD6126 (ANG453), Oxi-4503, BPI-2358 (plinabulin), MN029 (denibulin), EPC-2407 (crinobulin), ZIO-301 (indibulin), T115, BPROL075, ABT-751. These and other tubulin polymerization inhibitors are well described in the literature, e.g. in WO2011/151423, and in European J. Med. Chem., 87(2014) 89-124 which are hereby incorporated by reference.

Plinabulin (BPI-2358) is a small molecule currently undergoing clinical development for treating cancer, primarily non-small cell lung cancer. Plinabulin selectively binds to tubulin monomers and thereby prevents the polymerization of tubulin.

Plinabulin is a chemical compound having the structure:

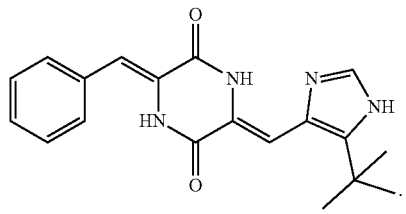 [SMILES: CC(C)(C)c1[nH]cnc1/C=c1\[nH]c(=O)/c(=C/c2ccccc2)[nH]c1=O]

Details of OC are provided in inter alia Reid et al., Cancer Biol Med 2017, doi:10.20892/j.issn.2095-3941,2016.0084; Koshiyama et al., BioMed Research International 2014 10.1155/2014/934261; and Chen et al. CANCER Supplement, May 15, 2003, Vol 97, Number 10. The main treatments for OC are surgery and chemotherapy, with almost all women undergoing surgery. While women with very early stage OC may only require surgery, the majority of patients present at an advanced stage and therefore require a combination of surgery and chemotherapy.

First line therapy: First line therapy for patients with epithelial OC is a combination of a tubulin inhibitor drug (e.g. paclitaxel) and a DNA cross-linking (platinum) drug (e.g. carboplatin, cisplatin). Paclitaxel suppresses tumour cell proliferation by inhibiting tubulin depolymerisation. The cytotoxic activity of platinum compounds is mediated through its binding with DNA and the production of intra- and inter-strand crosslinks, as well as the formation of adducts that cause conformational changes in DNA. This subsequently impairs replication and inhibits DNA synthesis leading to cell death. There is considerable heterogeneity with regard to overall drug sensitivity, but patients with recurrent OC eventually develop platinum- and/or platinum/paclitaxel—resistant disease.

Second line therapy: Current second line therapy to refractory OC is dependent on resistance mechanisms and different combinations of different cytotoxic agents, targeted agents and anti-angiogenesis biologic drugs (e.g. gemcitabine, bevacizumab, etopside, olaparib (PARP inhibitor), topotecan and doxorubicine) are being used with limited therapeutic efficacy. The relative 5-year OC survival is poor, especially for the women diagnosed with advanced disease due to multidrug resistance. Thus, there is a gap in the market to address this huge unmet medical need for novel second line therapy for this patient group. The need to develop new therapies for the effective treatment of OC is thus urgent. Objectives, the associated solutions and their advantages follow with the description, examples and claims.

DESCRIPTION OF THE INVENTION

The present invention relates to methods of treating, preventing or alleviating cancer, comprising administering to a subject in need thereof (i) a therapeutically effective amount of a tubulin polymerization inhibitor or a pharmaceutically acceptable salt, hydrate, solvate or amorphous solid thereof, and (ii) a therapeutically effective amount of a poly (ADP-ribose) polymerase (PARP) inhibitor or a pharmaceutically acceptable salt, hydrate, solvate or amorphous solid thereof.

In one embodiment, the tubulin polymerization inhibitor is a compound of formula I, or a pharmaceutically acceptable solvate or salt thereof.

Accordingly, in one embodiment, the present invention relates to methods of treating, preventing or alleviating cancer, comprising administering to a subject in need thereof (i) a therapeutically effective amount of a compound of formula I, or a pharmaceutically acceptable solvate or salt thereof, and (ii) a therapeutically effective amount of a poly (ADP-ribose) polymerase (PARP) inhibitor or a pharmaceutically acceptable salt, hydrate, solvate or amorphous solid thereof.

In one embodiment the invention provides a compound of formula I, or a pharmaceutically acceptable solvate or salt thereof, and a poly (ADP-ribose) polymerase (PARP) inhibitor, or a pharmaceutically acceptable salt, hydrate, solvate or amorphous solid thereof, in combination, for use in treatment of cancer;

wherein said formula I is represented by:

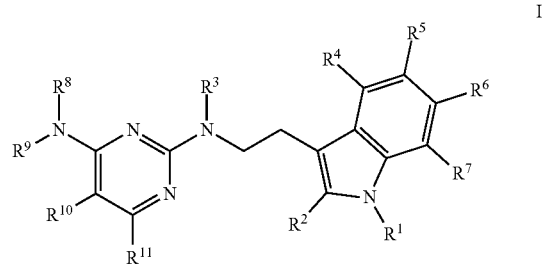

wherein
$R^1$, $R^3$, $R^8$, $R^{12}$, $R^{13}$, and $R^{14}$ represent hydrogen;
$R^2$ represents hydrogen or methyl;
$R^4$, $R^5$, $R^6$, and $R^7$ are independently selected from hydrogen, halogen, hydroxy, $(C_1-C_4)$alkyl, $O(C_1-C_4)$alkyl, $O(C_1-C_4)$alkyl$(C_2-C_5)$heterocyclyl, and $OCF_3$;
$R^{10}$ is selected from hydrogen, $(C_1-C_4)$alkyl and $NH_2$;
$R^{11}$ is selected from hydrogen, $(C_1-C_4)$alkyl, $(CO)NH_2$, and $(C_2-C_5)$heterocyclyl$(C_1-C_4)$alkyl;
$R^9$ is selected from:

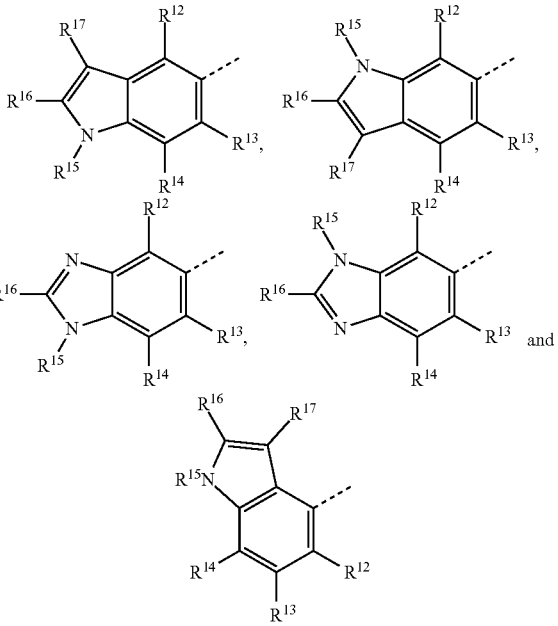

$R^{15}$ is selected from hydrogen and methyl; and
$R^{16}$ and $R^{17}$ are independently selected from hydrogen, $(C_1-C_4)$alkyl, $(C_1-C_4)$alkyl-OH, and $(CO)OH$.

In one embodiment, said compound of formula I is selected from:
$N^4$-(1H-indol-5-yl)-$N^2$-[2-(5-methoxy-1H-indol-3-yl)ethyl] pyrimidine-2,4-diamine;
$N^2$-[2-(1H-indol-3-yl)ethyl]-$N^4$-(2-methyl-1H-indol-5-yl) pyrimidine-2,4-diamine;
$N^2$-[2-(5-methoxy-1H-indol-3-yl)ethyl]-$N^4$-(2-methyl-1H-indol-5-yl)pyrimidine-2,4-diamine;
$N^2$-[2-(5-ethoxy-1H-indol-3-yl)ethyl]-$N^4$-(2-methyl-1H-indol-5-yl)pyrimidine-2,4-diamine;

$N^4$-(2-methyl-1H-indol-5-yl)-$N^2$-{2-[5-(trifluoromethoxy)-1H-indol-3-yl]ethyl}pyrimidine-2,4-diamine;
$N^2$-[2-(5-methyl-1H-indol-3-yl)ethyl]-$N^4$-(2-methyl-1H-indol-5-yl)pyrimidine-2,4-diamine;
$N^2$-[2-(5-fluoro-1H-indol-3-yl)ethyl]-$N^4$-(2-methyl-1H-indol-5-yl)pyrimidine-2,4-diamine;
$N^2$-[2-(6-methoxy-1H-indol-3-yl)ethyl]-$N^4$-(2-methyl-1H-indol-5-yl)pyrimidine-2,4-diamine;
$N^2$-[2-(7-methoxy-1H-indol-3-yl)ethyl]-$N^4$-(2-methyl-1H-indol-5-yl)pyrimidine-2,4-diamine;
$N^4$-(1,2-dimethyl-1H-indol-5-yl)-$N^2$-[2-(5-methoxy-1H-indol-3-yl)ethyl]pyrimidine-2,4-diamine;
$N^4$-(2,3-dimethyl-1H-indol-5-yl)-$N^2$-[2-(5-methoxy-1H-indol-3-yl)ethyl]pyrimidine-2,4-diamine;
(5-{2-[2-(5-methoxy-1H-indol-3-yl)ethylamino]pyrimidin-4-ylamino}-1H-indol-2-yl)methanol;
methyl 5-{2-[2-(5-methoxy-1H-indol-3-yl)ethylamino]pyrimidin-4-ylamino}-1H-indole-2-carboxylate;
$N^4$-(1H-benzo[d]imidazol-5-yl)-$N^2$-[2-(5-methoxy-1H-indol-3-yl)ethyl]pyrimidine-2,4-diamine;
$N^2$-[2-(5-methoxy-1H-indol-3-yl)ethyl]-$N^4$-(2-methyl-1H-benzo[d]imidazol-5-yl)pyrimidine-2,4-diamine;
$N^4$-(1H-indol-6-yl)-$N^2$-[2-(5-methoxy-1H-indol-3-yl)ethyl]pyrimidine-2,4-diamine;
$N^4$-(1H-indol-4-yl)-$N^2$-[2-(5-methoxy-1H-indol-3-yl)ethyl]pyrimidine-2,4-diamine;
$N^2$-[2-(1H-indol-3-yl)ethyl]-6-methyl-$N^4$-(2-methyl-1H-indol-5-yl)pyrimidine-2,4-diamine;
$N^2$-[2-(5-methoxy-1H-indol-3-yl)ethyl]-6-methyl-$N^4$-(2-methyl-1H-indol-5-yl)pyrimidine-2,4-diamine;
2-[2-(5-methoxy-1H-indol-3-yl)ethylamino]-6-(2-methyl-1H-indol-5-ylamino)pyrimidine-4-carboxamide; and
$N^2$-[2-(5-methoxy-1H-indol-3-yl)ethyl]-5-methyl-$N^4$-(2-methyl-1H-indol-5-yl)pyrimidine-2,4-diamine;
$N^2$-[2-(4-methoxy-1H-indol-3-yl)ethyl]-$N^4$-(2-methyl-1H-indol-5-yl)pyrimidine-2,4-diamine;
$N^4$-(2-methyl-1H-indol-5-yl)-$N^2$-[2-(5-propoxy-1H-indol-3-yl)ethyl]pyrimidine-2,4-diamine;
$N^2$-[2-(5-isopropoxy-1H-indol-3-yl)ethyl]-$N^4$-(2-methyl-1H-indol-5-yl)pyrimidine-2,4-diamine;
$N^2$-[2-(5,6-dimethoxy-1H-indol-3-yl)ethyl]-$N^4$-(2-methyl-1H-indol-5-yl)pyrimidine-2,4-diamine;
$N^2$-[2-(5-methoxy-7-methyl-1H-indol-3-yl)ethyl]-$N^4$-(2-methyl-1H-indol-5-yl)pyrimidine-2,4-diamine;
$N^2$-[2-(5-methoxy-1H-indol-3-yl)ethyl]-$N^4$-(1-methyl-1H-benzo[d]imidazol-5-yl)pyrimidine-2,4-diamine;
$N^4$-(1,2-dimethyl-1H-benzo[d]imidazol-5-yl)-$N^2$-[2-(5-methoxy-1H-indol-3-yl)ethyl]pyrimidine-2,4-diamine;
$N^2$-[2-(5-methoxy-1H-indol-3-yl)ethyl]-$N^4$-(1-methyl-1H-indol-4-yl)pyrimidine-2,4-diamine;
$N^2$-[2-(5-ethoxy-1H-indol-3-yl)ethyl]-6-methyl-$N^4$-(2-methyl-1H-indol-5-yl)pyrimidine-2,4-diamine;
$N^2$-[2-(5-methoxy-2-methyl-1H-indol-3-yl)ethyl]-6-methyl-$N^4$-(2-methyl-1H-indol-5-yl)pyrimidine-2,4-diamine;
$N^2$-[2-(5-methoxy-1H-indol-3-yl)ethyl]-6-methyl-$N^4$-(2-methyl-1H-benzo[d]imidazol-5-yl)pyrimidine-2,4-diamine;
$N^2$-[2-(5-ethoxy-1H-indol-3-yl)ethyl]-6-methyl-$N^4$-(2-methyl-1H-benzo[d]imidazol-5-yl)pyrimidine-2,4-diamine;
[5-(2-{[2-(5-methoxy-1H-indol-3-yl)ethyl][methyl]amino}pyrimidin-4-ylamino)-1H-indol-2-yl]methanol;
(5-{2-[2-(5-methoxy-1H-indol-3-yl)ethylamino]pyrimidin-4-ylamino}-1-methyl-1H-benzo[d]imidazol-2-yl)methanol;
$N^2$-[2-(5-methoxy-1H-indol-3-yl)ethyl]-$N^4$-methyl-$N^4$-(2-methyl-1H-indol-5-yl)pyrimidine-2,4-diamine;
$N^4$-(1,2-dimethyl-1H-indol-5-yl)-$N^2$-[2-(5-methoxy-1H-indol-3-yl)ethyl]-$N^4$-methylpyrimidine-2,4-diamine;
[5-({2-[2-(5-ethoxy-1H-indol-3-yl)ethylamino]pyrimidin-4-yl}amino)-1H-indol-2-yl]methanol;
$N^2$-[2-(5-methoxy-1H-indol-3-yl)ethyl]-$N^4$-(2-methyl-1H-indol-6-yl)pyrimidine-2,4-diamine;
$N^2$-[2-(5-ethoxy-1H-indol-3-yl)ethyl]-$N^4$-(2-methyl-1H-indol-6-yl)pyrimidine-2,4-diamine;
$N^2$-[2-(5-methoxy-1H-indol-3-yl)ethyl]-$N^4$-(1-methylindol-6-yl)pyrimidine-2,4-diamine;
$N^2$-[2-(5-ethoxy-1H-indol-3-yl)ethyl]-$N^4$-(1-methylindol-6-yl)pyrimidine-2,4-diamine;
$N^2$-[2-(5-methoxy-1H-indol-3-yl)ethyl]-$N^4$-(2-methyl-1H-indol-4-yl)pyrimidine-2,4-diamine;
$N^2$-[2-(5-ethoxy-1H-indol-3-yl)ethyl]-$N^4$-(2-methyl-1H-indol-4-yl)pyrimidine-2,4-diamine;
3-[2-({4-[(1-methylindol-4-yl)amino]pyrimidin-2-yl}amino)ethyl]-1H-indol-5-ol;
$N^2$-[2-(5-ethoxy-1H-indol-3-yl)ethyl]-$N^4$-(1-methylindol-4-yl)pyrimidine-2,4-diamine;
$N^4$-(1,2-dimethylindol-4-yl)-$N^2$-[2-(5-methoxy-1H-indol-3-yl)ethyl]pyrimidine-2,4-diamine;
$N^2$-[2-(5-methoxy-1H-indol-3-yl)ethyl]-$N^4$-(2-methyl-1H-benzimidazol-4-yl)pyrimidine-2,4-diamine;
$N^2$-[2-(5-ethoxy-1H-indol-3-yl)ethyl]-$N^4$-(2-methyl-1H-benzimidazol-4-yl)pyrimidine-2,4-diamine;
2-[2-(5-ethoxy-1H-indol-3-yl)ethylamino]-6-[(2-methyl-1H-indol-5-yl)amino]pyrimidine-4-carboxamide;
6-[(1,2-dimethylbenzimidazol-5-yl)amino]-2-[2-(5-methoxy-1H-indol-3-yl)ethylamino]pyrimidine-4-carboxamide;
2-[2-(5-methoxy-1H-indol-3-yl)ethylamino]-6-[(1-methylindol-4-yl)amino]pyrimidine-4-carboxamide;
2-[2-(5-ethoxy-1H-indol-3-yl)ethylamino]-6-[(1-methylindol-4-yl)amino]pyrimidine-4-carboxamide
$N^2$-[2-(5-methoxy-1H-indol-3-yl)ethyl]-$N^4$-(1-methylindol-4-yl)-6-(4-methylpiperazin-1-yl)pyrimidine-2,4-diamine; and
$N^2$-[2-(5-ethoxy-1H-indol-3-yl)ethyl]-$N^4$-(2-methyl-1H-indol-5-yl)pyrimidine-2,4,5-triamine.

In one embodiment, said compound of formula I is $N^2$-[2-(5-methoxy-1H-indol-3-yl)ethyl]-$N^4$-(1-methyl-1H-indol-4-yl)pyrimidine-2,4-diamine (NOV202).

NOV202 is a chemical compound with the following structure:

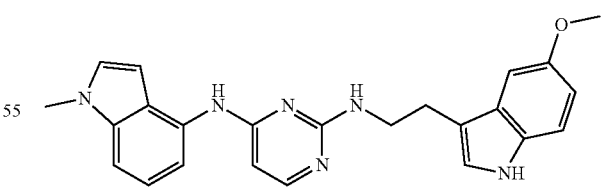

NOV202 has the following IUPAC nomenclature: $N^2$-[2-(5-methoxy-1H-indol-3-yl)ethyl]-$N^4$-(1-methyl-1H-indol-4-yl)pyrimidine-2,4-diamine. Its structure and antitumor effects have been described in inter alia Rickardson et al., Drug Design, Development and Therapy 2017: 11, 1335-1351 and WO 2012/127032. Methods of synthesizing compounds of Formula I, including NOV202, are described in WO 2012/127032.

Compounds of Formula I, including NOV202, exerts its action by inhibition of tubulin polymerization and thereby the assembly of microtubule structures, which cause a cell cycle arrest and cell death via apoptosis. NOV202 has been shown to have potent anti-proliferative activity in a panel of human cancer cell lines, including both solid and hematological malignancies, and was shown to be very potent in the ovarian cancer (OC) cell line A2780. NOV202 has also been shown to be as effective in multidrug resistant OC cells as in the isogenic (drug sensitive variant) non-resistant OC cells. The A2780/Adr multidrug resistant OC cell line overexpresses the P-glycoprotein efflux transporters which confer multidrug resistance.

In additional experiments, NOV202 was also shown to be highly potent in causing cell death, indicating that NOV202 could be a potential therapy for women that relapse after first-line therapy of OC.

Development of the tumour vasculature system is essential to tumour growth and metastatic spread of malignant cells. The rationale behind using vasculature targeting agents in anti-cancer therapy is that the cancer cells will be deprived of essential nutrients and oxygen supply for their growth and spread, thereby improving treatment outcome. In vivo efficacy study in a human OC xenograft model shows that NOV202 potently suppresses tumour growth with up to 80%, similar to the "golden standard", paclitaxel, in this cancer model. The treatment was well tolerated when administered to the animals by oral gavage over a period of 20 days, suggesting low off-target toxicity.

In an alternative embodiment, the tubulin polymerization inhibitor is selected from combretastatin CA-4P (zybrestat), AVE-8062 (ombrabulin), BNC105P, MPC-6827 (azixa), ZD6126 (ANG453), Oxi-4503, BPI-2358 (plinabulin), MN029 (denibulin), EPC-2407 (crinobulin), ZIO-301 (indibulin), T115, BPROL75 and ABT-751 or a pharmaceutically acceptable solvate or salt thereof.

Typically according to this embodiment, the tubulin polymerization inhibitor is plinabulin, i.e. a compound of formula II, or a pharmaceutically acceptable solvate or salt thereof.

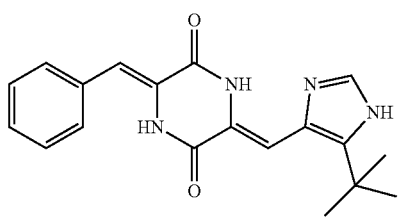

II

Accordingly, in one embodiment, the invention provides olaparib or a pharmaceutically acceptable solvate or salt thereof, plinabulin, or a pharmaceutically acceptable salt, hydrate, solvate or amorphous solid thereof, in combination, for use in treatment of cancer. Embodiments of this aspect are the same as for the embodiments of the first disclosed aspect above.

Methods and assays for identification and evaluation of potential tubulin polymerisation inhibitors are extensively described in the literature and many assays are commercially available. For example, a fluorescence-based assay can be used wherein polymerization of the tubulin is followed by fluorescence enhancement due to the incorporation of a fluorescent reporter into microtubules as polymerization occurs. The fluorescent assay is based upon the fact that light is scattered by microtubules to an extent that is proportional to the concentration of microtubule polymer. Tubulin polymerisation screening assays are described e.g. in Mol. Cell Biol. 25(2005), 4488-4500, Mol. Cancer Res; 11(8) August 2013, 856-864, and are also commercially available from e.g. Cytoskeleton Inc.

In one embodiment, said poly (ADP-ribose) polymerase (PARP) inhibitor is selected from olaparib, niraparib, veliparib, talazoparib, rucaparib, iniparib, fluzoparib, AZD2461, UPF 1069, PJ34, A-966492, AG-14361, E7449 and NMS-P118.

These and other PARP inhibitors are well described in the literature (Ohmoto, A. and Yachida, S., Onco Targets and Therapy 2017: 10, 5195-5208).

Assays for identification and evaluation of potential PARP inhibitors are extensively described in the literature and many assays are commercially available. For example, colorimetric assays for the screening of PARP inhibitors by measuring the incorporation of a unique biotinylated NAD substrate onto histone proteins can be used. The technology in these assays is ideal for the screening of inhibitors of PARP where the formation of poly(ADP-ribose) chains is inhibited.

Such assays are available from i.a. CosmoBio Co and from Trevigen®. Alternatively, a fluorescent screening assay may be used for the identification of PARP-1 inhibitors in an in vitro system. In this technique, the inhibitor is identified by an increase in fluorescent signal when PARP mediated NAD+ depletion is inhibited. Fluorescent screening assays are available from e.g. Trevigen®

In one embodiment, said poly (ADP-ribose) polymerase (PARP) inhibitor is olaparib Olaparib is a chemical compound with the following chemical structure:

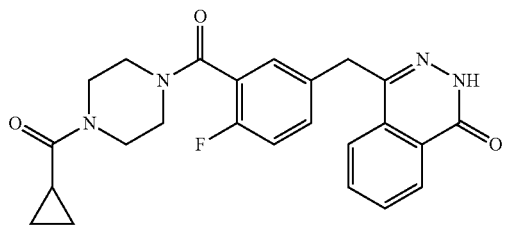 [SMILES: O=C(c1cc(Cc2n[nH]c(=O)c3ccccc23)ccc1F)N1CCN(C(=O)C2CC2)CC1]

Olaparib has the following IUPAC nomenclature: 4-(3-{[4-(cyclopropylcarbonyl)piperazin-1-yl]carbonyl}-4-fluorobenzyl)phthalazin-1(2H)-one. Olaparib is a Poly(ADP-ribose) polymerase (PARP) inhibitor and is known as useful in treatment BRCA deficient ovarian cancer (Meehan and Chen, Gynecologic Oncology Research and Practice (2016) 3:3). Suggested mechanisms of action for olaparib are discussed inter alia in Yang et al., Sci Transl. Med. 9 eaal 1645, 2017.

In one embodiment, said cancer is a primary tumor.
In one embodiment, said cancer is a metastasis.
In one embodiment, said cancer is a solid tumor.
In one embodiment, said cancer is a BRCA mutated tumor.
In one embodiment, said cancer is a BRCA mutated breast, ovarian, prostate or pancreas cancer.
In one embodiment, said cancer is a p53 suppressor gene mutated tumor.
In one embodiment, said cancer is a p53 mutated breast, ovarian, prostate, lung, brain or pancreas cancer.

In one embodiment, said cancer is a p53 missense mutated tumor with expression of the full-length mutant p53 protein.

In one embodiment, said cancer is a p53 missense mutated breast, ovarian, prostate, lung, brain or pancreas cancer with expression of the full-length mutant p53 protein.

In one embodiment, said cancer is a homologous recombination repair defect tumor with mutations in repair genes other than BRCA1/BRCA2.

In one embodiment, said cancer is a homologous recombination repair defect breast, ovarian, prostate, lung, brain or pancreas cancer with mutations in repair genes other than BRCA1/BRCA2.

In one embodiment, said cancer is a homologous recombination repair defect tumor with mutations in repair genes other than BRCA1/BRCA2, such as ATM, ATR, PALB2, RAD51, CHEK1 and CHEK2, as well as epigenetic loss of BRCA1 function through promoter methylation.

In one embodiment, said cancer is a homologous recombination repair defect breast, ovarian, prostate, lung, brain or pancreas cancer with mutations in repair genes other than BRCA1/BRCA2, such as ATM, ATR, PALB2, RAD51, CHEK1 and CHEK2, as well as epigenetic loss of BRCA1 function through promoter methylation.

In one embodiment, said cancer is selected from the group consisting of breast cancer, lung cancer, ovarian cancer, endometrial cancer, prostate cancer, pharyngeal cancer, esophageal cancer, glioblastoma, adrenal cancer, B-cell malignancies, biliary tract cancer, bladder cancer, bone cancer, brain cancer, cervical cancer, choriocarcinoma, colon cancer, colorectal cancer, connective tissue cancer, cancer of the digestive system, gallbladder cancer, gastric cancer, cancer of the head and neck, hepatocellular carcinoma, intra-epithelial neoplasm, kidney cancer, liver cancer, lymphoma, skin cancer, neuroblastoma, mesothelioma, neuroglioma, oral cavity cancer, pediatric cancer, pancreatic cancer, pancreatic endocrine tumors, pituitary adenoma, thymoma, renal cell carcinoma, cancer of the respiratory system, salivary gland cancer, sarcoma, small bowel cancer, testicular cancer, thyroid cancer, ureteral cancer, cancer of the urinary system, and hematological cancer.

In one embodiment, said cancer is ovarian cancer. Said ovarian cancer may be a BRCA mutated ovarian cancer.

Said breast cancer may be selected from estrogen receptor positive or negative, progesterone receptor positive or negative, HER-2 positive or negative, triple-negative breast cancer, or BRCA1 and/or BRCA2 positive or negative breast cancer.

Said lung cancer may be selected from non-small cell lung cancer and small cell lung cancer.

Said skin cancer may be selected from melanoma and basal cell carcinoma.

Said sarcoma may be selected from Ewing's sarcoma, fibrosarcoma, and rhabdomyosarcoma.

Said hematological cancer may be selected from leukemia, lymphoma and multiple myeloma.

In one embodiment, said compound of formula I is $N^2$-[2-(5-methoxy-1H-indol-3-yl)ethyl]-$N^4$-(1-methyl-1H-indol-4-yl)pyrimidine-2,4-diamine (NOV202); said poly (ADP-ribose) polymerase (PARP) inhibitor is olaparib; and said cancer is ovarian cancer.

As used herein, the term "NOV202" denotes the compound with the IUPAC name $N^2$-[2-(5-methoxy-1H-indol-3-yl)ethyl]-$N^4$-(1-methyl-1H-indol-4-yl)pyrimidine-2,4-diamine.

As used herein, the term "olaparib" or "Olaparib" denotes the compound with the IUPAC name 4-(3-{[4-(cyclopropylcarbonyl)piperazin-1-yl]carbonyl}-4-fluorobenzyl)phthalazin-1(2H)-one.

As used herein, the term "plinabulin" or "Plinabulin" denotes the compound with the IUPAC name (3Z,6Z)-3-Benzylidene-6-{[5-(2-methyl-2-propanyl)-1H-imidazol-4-yl]methylene}-2,5-piperazinedione.

As used herein, the term "preventing" includes, but is not limited to, inhibiting and/or averting one or more biochemical changes, histologic changes, and/or behavioral symptoms associated with ovarian cancer.

As used herein, "treatment" or "treating" is an approach for obtaining beneficial and/or desired results, including, but not limited to, clinical results. Non-limiting examples of beneficial and/or desired results include one or more of the following: increasing the quality of life, decreasing the dose of one or more other medications required to treat the disease, delaying the progression of the disease, altering the underlying disease process and/or course, and/or prolonging survival.

As used herein, the terms "effective amount" and "therapeutically effective amount" refer to an amount of a compound or pharmaceutical composition sufficient to produce a desired therapeutic effect including, but not limited to, preventing, and/or delaying onset and/or development of at least one disease. The therapeutically effective amount can vary depending upon the intended application, the subject to be treated (including, e.g., weight and age), the disease and its severity, the route and timing of administration, the desired effect (e.g., lower side effect(s)), the dosing regimen to be used, and the formulation and delivery system (if any).

In some embodiments, the "therapeutic effective amount" of a drug used in combination with at least one other therapeutic agent may be the same as or different from (either lower or higher) the "therapeutic effective amount" of the drug used individually (i.e., in a monotherapy).

In one embodiment, said tubulin polymerization inhibitor is administered at a dose ranging from 0.5 to 50 mg/kg per day. The tubulin polymerization inhibitor may be e.g. plinabulin.

In one embodiment, said compound of formula I is administered at a dose ranging from 0.5 to 50 mg/kg per day.

In one embodiment, said poly (ADP-ribose) polymerase (PARP) inhibitor is administered at a dose ranging from 0.5 to 100 mg/kg per day.

In one embodiment, said tubulin polymerization inhibitor and/or said poly (ADP-ribose) polymerase (PARP) inhibitor is administered by intravenous infusion. The tubulin polymerization inhibitor may be e.g. plinabulin.

In one embodiment, said compound of formula I and/or said poly (ADP-ribose) polymerase (PARP) inhibitor is administered by intravenous infusion.

In one embodiment, said tubulin polymerization inhibitor and/or said poly (ADP-ribose) polymerase (PARP) inhibitor is administered orally. The tubulin polymerization inhibitor may be e.g. plinabulin.

In one embodiment, said compound of formula I and/or said poly (ADP-ribose) polymerase (PARP) inhibitor is administered orally.

In one embodiment, said tubulin polymerization inhibitor and said poly (ADP-ribose) polymerase (PARP) inhibitor is administered once daily, during a 14-day cycle. The tubulin polymerization inhibitor is e.g. plinabulin.

In one embodiment, said compound of formula I and said poly (ADP-ribose) polymerase (PARP) inhibitor is administered once daily, during a 14-day cycle.

In one aspect of the invention, there is provided a pharmaceutical composition for use in treatment of ovarian cancer, comprising a tubulin polymerization inhibitor or a pharmaceutically acceptable salt thereof, and a therapeutically effective amount of olaparib or a pharmaceutically acceptable salt thereof.

In one embodiment of the invention, there is provided a pharmaceutical composition for use in treatment of ovarian cancer, comprising NOV202 or a pharmaceutically acceptable salt thereof, and a therapeutically effective amount of olaparib or a pharmaceutically acceptable salt thereof.

In one embodiment of the invention, there is provided a pharmaceutical composition for use in treatment of ovarian cancer, comprising plinabulin or a pharmaceutically acceptable salt thereof, and a therapeutically effective amount of olaparib or a pharmaceutically acceptable salt thereof.

The invention additionally provides a method of treating, preventing or alleviating cancer, comprising administering to a subject in need thereof (i) a therapeutically effective amount of a tubulin polymerization inhibitor or a pharmaceutically acceptable solvate or salt thereof, and (ii) a therapeutically effective amount of a poly (ADP-ribose) polymerase (PARP) inhibitor, or a pharmaceutically acceptable salt, hydrate, solvate or amorphous solid thereof.

In one embodiment, the tubulin polymerization inhibitor is a compound of formula I, or a pharmaceutically acceptable solvate or salt thereof, Accordingly, the invention provides a method of treating, preventing or alleviating cancer, comprising administering to a subject in need thereof (i) a therapeutically effective amount of a compound of formula I or a pharmaceutically acceptable solvate or salt thereof, and (ii) a therapeutically effective amount of a poly (ADP-ribose) polymerase (PARP) inhibitor, or a pharmaceutically acceptable salt, hydrate, solvate or amorphous solid thereof;

wherein said formula I is represented by:

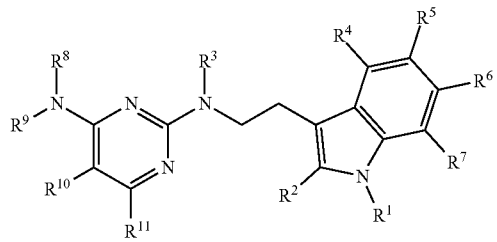

I wherein
$R^1$, $R^3$, $R^8$, $R^{12}$, $R^{13}$, and $R^{14}$ represent hydrogen;
$R^2$ represents hydrogen or methyl;
$R^4$, $R^5$, $R^6$, and $R^7$ are independently selected from hydrogen, halogen, hydroxy, $(C_1-C_4)$alkyl, $O(C_1-C_4)$alkyl, $O(C_1-C_4)$alkyl$(C_2-C_5)$heterocyclyl, and $OCF_3$;
$R^{10}$ is selected from hydrogen, $(C_1-C_4)$alkyl and $NH_2$;
$R^{11}$ is selected from hydrogen, $(C_1-C_4)$alkyl, $(CO)NH_2$, and $(C_2-C_5)$heterocyclyl$(C_1-C_4)$alkyl;
$R^9$ is selected from:

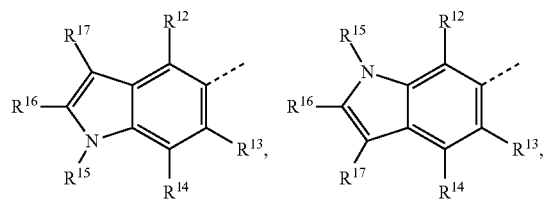

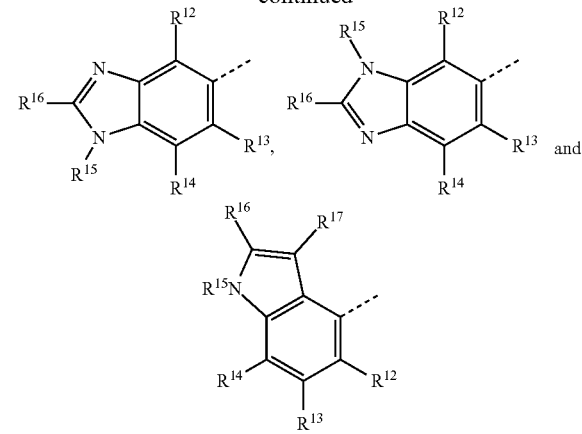

$R^{15}$ is selected from hydrogen and methyl; and
$R^{16}$ and $R^{17}$ are independently selected from hydrogen, $(C_1-C_4)$alkyl, $(C_1-C_4)$alkyl-OH, and $(CO)OH$.

In an alternative embodiment, the tubulin polymerization inhibitor is selected from combretastatin CA-4P (zybrestat), AVE-8062 (ombrabulin), BNC105P, MPC-6827 (azixa), ZD6126 (ANG453), Oxi-4503, BPI-2358 (plinabulin), MN029 (denibulin), EPC-2407 (crinobulin), ZIO-301 (indibulin), T115, BPROL75 and ABT-751 or a pharmaceutically acceptable solvate or salt thereof.

Typically according to this embodiment, the tubulin polymerization inhibitor is plinabulin, i.e. a compound of formula II, or a pharmaceutically acceptable solvate or salt thereof.

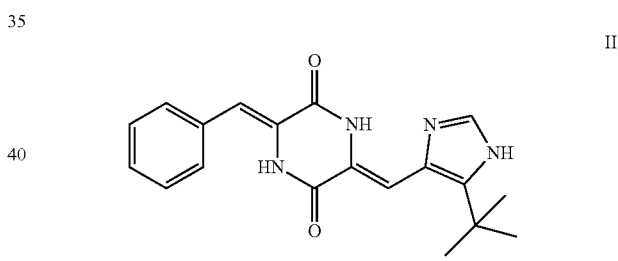

II

Accordingly, the invention provides a method of treating, preventing or alleviating cancer, comprising administering to a subject in need thereof (i) a therapeutically effective amount of olaparib, or a pharmaceutically acceptable solvate or salt thereof, and (ii) a therapeutically effective amount of plinabulin, or a pharmaceutically acceptable salt, hydrate, solvate or amorphous solid thereof.

Embodiments of this aspect are the same as for the embodiments of the aspect disclosed above. Said subject is typically a mammalian subject, including human subjects.

In some embodiments, the combination therapies disclosed herein may comprise lower doses of one or more of the individual therapies than would be necessary if the individual therapies are given alone (i.e. tubulin polymerization inhibitor, and PARP inhibitor monotherapies). This decreased dose may reduce one or more side-effects associated with the therapies. For example, in some embodiments, the same or greater therapeutic benefit is achieved using a smaller amount (e.g., a lower dose or a less frequent dosing schedule) of said tubulin polymerization inhibitor, and said PARP inhibitor, or both, in the combination therapy than the amount(s) generally used for individual therapy.

Further as an example, in some embodiments, the use of a small amount of said tubulin polymerization inhibitor, said PARP inhibitor, or both results in a reduction in the number, severity, frequency and/or duration of one or more side-effects associated with the compounds. As non-limiting examples, the combination therapy may comprise, compared to the doses generally used for individual therapies: (i) lower dose of said tubulin polymerization inhibitor and lower dose of said PARP inhibitor; (ii) lower dose of said tubulin polymerization inhibitor and the same dose of said PARP inhibitor; (iii) lower dose of said PARP inhibitor and the same dose of said tubulin polymerization inhibitor. The tubulin polymerization inhibitor may be e.g. plinabulin.

In some embodiments, the combination therapies disclosed herein may comprise lower doses of one or more of the individual therapies than would be necessary if the individual therapies are given alone (i.e. compound of formula I, and PARP inhibitor monotherapies). This decreased dose may reduce one or more side-effects associated with the therapies. For example, in some embodiments, the same or greater therapeutic benefit is achieved using a smaller amount (e.g., a lower dose or a less frequent dosing schedule) of said compound of formula I, and said PARP inhibitor, or both, in the combination therapy than the amount(s) generally used for individual therapy. Further as an example, in some embodiments, the use of a small amount of said compound of formula I, said PARP inhibitor, or both results in a reduction in the number, severity, frequency and/or duration of one or more side-effects associated with the compounds. As non-limiting examples, the combination therapy may comprise, compared to the doses generally used for individual therapies: (i) lower dose of said compound of formula I and lower dose of said PARP inhibitor; (ii) lower dose of said compound of formula I and the same dose of said PARP inhibitor; (iii) lower dose of said PARP inhibitor and the same dose of said compound of formula I.

In some embodiments, the combination therapies disclosed herein may comprise higher doses of the individual therapies than would be necessary if the individual therapies were given alone (i.e., said tubulin polymerization inhibitor and said PARP inhibitor monotherapies). For example, in some embodiments of the combination therapies, the dose of one of the drugs (tubulin polymerization inhibitor or PARP inhibitor) is lower than its dose generally used for individual therapy, while the other drug is given at an equal or higher dose than its dose generally used for individual therapy. As non-limiting examples, the combination therapy may comprise (i) higher dose of said PARP inhibitor and lower dose of said tubulin polymerization inhibitor; or (ii) higher dose of said tubulin polymerization inhibitor and lower dose of said PARP inhibitor. In some instances, increasing the dose of one of the drugs while decreasing the dose of the other may have one or both advantages of alleviating the side effects of the drug with lower dose and obtaining the same or greater therapeutic benefit than individual therapies. Further, as an example, in some embodiments, the combination therapy may comprise, compared to the dosages generally used for individual therapies, (i) higher dose of said PARP inhibitor and higher dose of said tubulin polymerization inhibitor; (ii) higher dose of said tubulin polymerization inhibitor and the same dose of said PARP inhibitor; or (iii) higher dose of said PARP inhibitor and the same dose of said tubulin polymerization inhibitor. The tubulin polymerization inhibitor may be e.g. plinabulin.

In some embodiments, the combination therapies disclosed herein may comprise higher doses of the individual therapies than would be necessary if the individual therapies were given alone (i.e., said compound of formula I and said PARP inhibitor monotherapies). For example, in some embodiments of the combination therapies, the dose of one of the drugs (compound of formula I or PARP inhibitor) is lower than its dose generally used for individual therapy, while the other drug is given at an equal or higher dose than its dose generally used for individual therapy. As non-limiting examples, the combination therapy may comprise (i) higher dose of said PARP inhibitor and lower dose of said compound of formula I; or (ii) higher dose of said compound of formula I and lower dose of said PARP inhibitor. In some instances, increasing the dose of one of the drugs while decreasing the dose of the other may have one or both advantages of alleviating the side effects of the drug with lower dose and obtaining the same or greater therapeutic benefit than individual therapies. Further, as an example, in some embodiments, the combination therapy may comprise, compared to the dosages generally used for individual therapies, (i) higher dose of said PARP inhibitor and higher dose of said compound of formula I; (ii) higher dose of said compound of formula I and the same dose of said PARP inhibitor; or (iii) higher dose of said PARP inhibitor and the same dose of said compound of formula I.

In some embodiments, the combination therapy disclosed herein reduces the severity of one or more symptoms associated with ovarian cancer by at least 10%, 20%, 30%, 40%, 50%, 60%, 70%, 80%, 90%, or 95% or more, as compared to the corresponding symptom in the same subject prior to treatment or as compared to the corresponding symptom in other subjects not receiving the combination therapy. For example, in some embodiments, the administration of the tubulin polymerization inhibitor and said PARP inhibitor results in a reduction of the decline in the measure of ovarian cancer, such as at least 10%, 20%, 30%, 40%, 50%, 60%, 70%, 80%, 90%, or 95% or more, as compared to a control. In some embodiments, the administration of the combination of said compound of formula I and said PARP inhibitor results in a reduction of the decline in the measure of ovarian cancer, such as at least 10%, 20%, 30%, 40%, 50%, 60%, 70%, 80%, 90%, or 95% or more, as compared to a control.

In some embodiments, combinations of said tubulin polymerization inhibitor and said PARP inhibitor may be administered to a subject in a single dosage form and/or by separate administration of each active agent. The tubulin polymerization inhibitor may be e.g. plinabulin.

In some embodiments, combinations of said compound of formula I and said PARP inhibitor may be administered to a subject in a single dosage form and/or by separate administration of each active agent.

In some embodiments, said tubulin polymerization inhibitor and said PARP inhibitor may be formulated into a tablet, pill, capsule, or solution. The formulation of tubulin polymerization inhibitor and said PARP inhibitor may be selected appropriately. In some embodiments, said tubulin polymerization inhibitor, said PARP inhibitor or both are formulated into a solution for parenteral administration. In some embodiments, said tubulin polymerization inhibitor and said PARP inhibitor may be formulated in segregated regions or distinct caplets of housed within a capsule. In some embodiments, said tubulin polymerization inhibitor and said PARP inhibitor may be formulated in isolated layers in a tablet. The tubulin polymerization inhibitor may be e.g. plinabulin.

In some embodiments, said compound of formula I and said PARP inhibitor may be formulated into a tablet, pill, capsule, or solution. The formulation of said compound of formula I and said PARP inhibitor may be selected appropriately. In some embodiments, said compound of formula I, said PARP inhibitor or both are formulated into a solution for parenteral administration. In some embodiments, said compound of formula I and said PARP inhibitor may be formulated in segregated regions or distinct caplets of housed within a capsule. In some embodiments, said compound of formula I and said PARP inhibitor may be formulated in isolated layers in a tablet.

In some embodiments, the pharmaceutical composition for treating, preventing, and/or delaying onset and/or development of ovarian cancer comprises a therapeutically effective amount of said tubulin polymerization inhibitor, a therapeutically effective amount of said PARP inhibitor, and at least one pharmaceutically acceptable carrier. The tubulin polymerization inhibitor may be e.g. plinabulin.

In some embodiments, the pharmaceutical composition for treating, preventing, and/or delaying onset and/or development of ovarian cancer comprises a therapeutically effective amount of said compound of formula I, a therapeutically effective amount of said PARP inhibitor, and at least one pharmaceutically acceptable carrier.

In some embodiments, said tubulin polymerization inhibitor and said PARP inhibitor may be administered as separate compositions and optionally as different forms, e.g., as separate tablets or solutions. For example, in some embodiments, said PARP inhibitor is administered as once daily oral tablets and said tubulin polymerization inhibitor is administered as once daily oral tablets. Further as a non-limiting example, both said tubulin polymerization inhibitor and said PARP inhibitor are administered, separately, as oral tablets. Also further as a non-limiting example, both said tubulin polymerization inhibitor and said PARP inhibitor are administered separately, as injections. The tubulin polymerization inhibitor may be e.g. plinabulin.

In some embodiments, said compound of formula I and said PARP inhibitor may be administered as separate compositions and optionally as different forms, e.g., as separate tablets or solutions. For example, in some embodiments, said PARP inhibitor is administered as once daily oral tablets and said compound of formula I is administered as once daily oral tablets. Further as a non-limiting example, both said compound of formula I and said PARP inhibitor are administered, separately, as oral tablets. Also further as a non-limiting example, both said compound of formula I and said PARP inhibitor are administered separately, as injections.

In some embodiments, when said tubulin polymerization inhibitor and said PARP inhibitor are administered as separate compositions:

the pharmaceutical composition for use in combination with said PARP inhibitor for treating, preventing, and/or delaying the onset and/or development of cancer comprising a therapeutically effective amount of said tubulin polymerization inhibitor and at least one pharmaceutically acceptable carrier is administered separately; and the pharmaceutical composition for use in combination with said tubulin polymerization inhibitor for treating, preventing, and/or delaying the onset and/or development of cancer comprising a therapeutically effective amount of said PARP inhibitor and at least one pharmaceutically acceptable carrier is administered separately.

In some embodiments, when said compound of formula I and said PARP inhibitor are administered as separate compositions:

the pharmaceutical composition for use in combination with said PARP inhibitor for treating, preventing, and/or delaying the onset and/or development of cancer comprising a therapeutically effective amount of said compound of formula I and at least one pharmaceutically acceptable carrier is administered separately; and the pharmaceutical composition for use in combination with said compound of formula I for treating, preventing, and/or delaying the onset and/or development of cancer comprising a therapeutically effective amount of said PARP inhibitor and at least one pharmaceutically acceptable carrier is administered separately.

In one aspect of the invention, there is provided a kit for use in treating cancer or decreasing tumor size, said kit comprising (i) a tubulin polymerization inhibitor or a pharmaceutically acceptable solvate or salt thereof; and (ii) a poly (ADP-ribose) polymerase (PARP) inhibitor, or a pharmaceutically acceptable salt, hydrate, solvate or amorphous solid thereof. The tubulin polymerization inhibitor may be e.g. plinabulin.

In one embodiment, there is provided a kit for use in treating cancer or decreasing tumor size, said kit comprising (i) a compound of formula I or a pharmaceutically acceptable solvate or salt thereof; and (ii) a poly (ADP-ribose) polymerase (PARP) inhibitor, or a pharmaceutically acceptable salt, hydrate, solvate or amorphous solid thereof.

In one embodiment, said compound of formula I is $N^2$-[2-(5-methoxy-1H-indol-3-yl)ethyl]-$N^4$-(1-methyl-1H-indol-4-yl)pyrimidine-2,4-diamine (NOV202); said poly (ADP-ribose) polymerase (PARP) inhibitor is olaparib; and said cancer is ovarian cancer.

In an alternative embodiment, said tubulin polymerization inhibitor is plinabulin; said poly (ADP-ribose) polymerase (PARP) inhibitor is olaparib; and said cancer is ovarian cancer.

In some embodiments, said tubulin polymerization inhibitor and said PARP inhibitor may be administered simultaneously. In some embodiments, said tubulin polymerization inhibitor and said PARP inhibitor may be administered sequentially. In some embodiments, said tubulin polymerization inhibitor and said PARP inhibitor may be administered intermittently. The length of time between administrations of said tubulin polymerization inhibitor and said PARP inhibitor may be adjusted to achieve the desired therapeutic effect. In some embodiments, said tubulin polymerization inhibitor and said PARP inhibitor may be administered only a few minutes apart. In some embodiments, said tubulin polymerization inhibitor and said PARP inhibitor may be administered several hours (e.g., about 2, 4, 6, 10, 12, 24, or 36 h) apart. In some embodiments, it may be advantageous to administer more than one dosage of one of said tubulin polymerization inhibitor and said PARP inhibitor between administrations of the remaining therapeutic agent. For example, one therapeutic agent may be administered at 1 hour and then again at 11 hours following administration of the other therapeutic agent. In some embodiments, the therapeutic effects of each said tubulin polymerization inhibitor and said PARP inhibitor should overlap for at least a portion of the duration, so that the overall therapeutic effect of the combination therapy may be attributable in part to the combined or synergistic effects of the combination therapy. The tubulin polymerization inhibitor may be e.g. plinabulin.

In some embodiments, said compound of formula I and said PARP inhibitor may be administered simultaneously. In some embodiments, said compound of formula I and said PARP inhibitor may be administered sequentially. In some embodiments, said compound of formula I and said PARP inhibitor may be administered intermittently. The length of time between administrations of said compound of formula I and said PARP inhibitor may be adjusted to achieve the desired therapeutic effect. In some embodiments, said compound of formula I and said PARP inhibitor may be administered only a few minutes apart. In some embodiments, said compound of formula I and said PARP inhibitor may be administered several hours (e.g., about 2, 4, 6, 10, 12, 24, or 36 h) apart. In some embodiments, it may be advantageous to administer more than one dosage of one of said compound of formula I and said PARP inhibitor between administrations of the remaining therapeutic agent. For example, one therapeutic agent may be administered at 1 hour and then again at 11 hours following administration of the other therapeutic agent. In some embodiments, the therapeutic effects of each said compound of formula I and said PARP inhibitor should overlap for at least a portion of the duration, so that the overall therapeutic effect of the combination therapy may be attributable in part to the combined or synergistic effects of the combination therapy.

The dosage of said tubulin polymerization inhibitor and said PARP inhibitor may be dependent upon a number of factors including pharmacodynamic characteristics of each agent, mode route of administration, the health of the patient being treated, the extent of treatment desired, the nature and kind of concurrent therapy, if any, the frequency of treatment, and the nature of the effect desired. In some embodiments, said tubulin polymerization inhibitor may be administered at a dose ranging from 0.001 mg/kg body weight per day to 100 mg/kg body weight per day. In some embodiments, said PARP inhibitor may be administered at a dose ranging from 5 mg/day to 1200 mg/day, 5 mg/day to 500 mg/day, 10 mg/day to 75 mg/day, 5 mg/day to 50 mg/day, 15 mg/day to 50 mg/day, or 200 mg/day to 400 mg/day. In some embodiments, said PARP inhibitor may be administered at a dose ranging from about 5 mg/day to about 100 mg/day, about 10 mg/day to about 75 mg/day, about 5 mg/day to about 50 mg/day, about 15 mg/day to about 50 mg/day, or about 200 mg/day to about 400 mg/day. In some embodiments, said PARP inhibitor may be administered at a dose of 5 mg/day, 10 mg/day, 15 mg/day, 20 mg/day, 25 mg/day, 30 mg/day, 50 mg/day, 75 mg/day, 100 mg/day, 200 mg/day, 400 mg/day dosage or 1200 mg/day. The tubulin polymerization inhibitor may be e.g. plinabulin.

The dosage of said compound of formula I and said PARP inhibitor may be dependent upon a number of factors including pharmacodynamic characteristics of each agent, mode route of administration, the health of the patient being treated, the extent of treatment desired, the nature and kind of concurrent therapy, if any, the frequency of treatment, and the nature of the effect desired. In some embodiments, said compound of formula I may be administered at a dose ranging from 0.001 mg/kg body weight per day to 100 mg/kg body weight per day. In some embodiments, said PARP inhibitor may be administered at a dose ranging from 5 mg/day to 500 mg/day, 10 mg/day to 75 mg/day, 5 mg/day to 50 mg/day, 15 mg/day to 50 mg/day, or 200 mg/day to 400 mg/day. In some embodiments, said PARP inhibitor may be administered at a dose ranging from about 5 mg/day to about 100 mg/day, about 10 mg/day to about 75 mg/day, about 5 mg/day to about 50 mg/day, about 15 mg/day to about 50 mg/day, or about 200 mg/day to about 400 mg/day. In some embodiments, said PARP inhibitor may be administered at a dose of 5 mg/day, 10 mg/day, 15 mg/day, 20 mg/day, 25 mg/day, 30 mg/day, 50 mg/day, 75 mg/day, 100 mg/day, 200 mg/day, or 400 mg/day dosage.

In some embodiments, said PARP inhibitor may be administered at a dose ranging from 5 mg/day to 1200 mg/day In some embodiments, said PARP inhibitor may be administered at a dose of 1200 mg/day.

In some embodiments, said tubulin polymerization inhibitor may be administered at a dose ranging from 1 mg/kg to 50 mg/kg, 2.5 mg/kg to 30 mg/kg, 2.5 mg/kg to 5 mg/kg, or 5 mg/kg to 10 mg/kg. In some embodiments, said tubulin polymerization inhibitor is administered at a dose of 10 mg/kg every 2 weeks. In some embodiments, said compound of formula I is administered at a dose of 5 mg/kg every 2 weeks. In some embodiments, said tubulin polymerization inhibitor is administered at a dose of 2.5 mg/kg every 2 weeks. In some embodiments, said tubulin polymerization inhibitor is administered at a dose of 5 mg/kg every month. In some embodiments, said tubulin polymerization inhibitor is administered at a dose of 10 mg/kg every month. The tubulin polymerization inhibitor may be e.g. plinabulin.

In some embodiments, said compound of formula I may be administered at a dose ranging from 1 mg/kg to 50 mg/kg, 2.5 mg/kg to 30 mg/kg, 2.5 mg/kg to 5 mg/kg, or 5 mg/kg to 10 mg/kg. In some embodiments, said compound of formula I is administered at a dose of 10 mg/kg every 2 weeks. In some embodiments, said compound of formula I is administered at a dose of 5 mg/kg every 2 weeks. In some embodiments, said compound of formula I is administered at a dose of 2.5 mg/kg every 2 weeks. In some embodiments, said compound of formula I is administered at a dose of 5 mg/kg every month. In some embodiments, said compound of formula I is administered at a dose of 10 mg/kg every month.

In some embodiments of the invention, the tubulin polymerization inhibitor is a compound of formula I. Preferably according to this embodiment, the compound of formula I is $N^2$-[2-(5-methoxy-1H-indol-3-yl)ethyl]-$N^4$-(1-methyl-1H-indol-4-yl)pyrimidine-2,4-diamine (NOV202). In alternative embodiments of the invention, the tubulin polymerization inhibitor is combretastatin CA-4P (zybrestat), AVE-8062 (ombrabulin), BNC105P, MPC-6827 (azixa), ZD6126 (ANG453), Oxi-4503, BPI-2358 (plinabulin), MN029 (denibulin), EPC-2407 (crinobulin), ZIO-301 (indibulin), T115 or BPROL075, ABT-751. Preferably according to this embodiment, the tubulin polymerization inhibitor is plinabulin.

Figure 1:
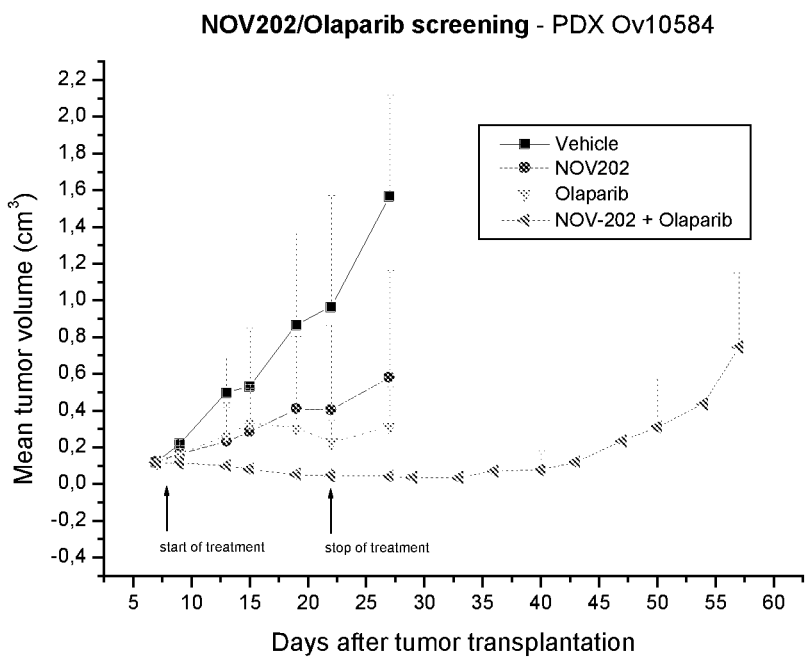
FIG. 1 sets out results of study of an in vivo anti-tumor efficacy of NOV202 alone and in combination with olaparib in a patient-derived xenograft of ovarian cancer. Details are provided in Example 1.

The invention will be described in the following, non-limiting examples.

EXAMPLE 1

A Study of Anti-Tumor Efficacy of NOV202 Alone and in Combination with Olaparib in a Patient-Derived Xenograft of Ovarian Cancer (Ov10584)

NMRI:nu/nu female (Janvier) mice (8 weeks old) were used as follows: 4 animals in the vehicle group, 4 animals in NOV202 group, Olaparib group and in the combination group of NOV202 and olaparib, respectively. NOV202 was synthesized as described in WO 2012/127032. Olaparib was purchased from LC Laboratories. The patient-derived xenograft Ov10584 was used at passage number 7. All mice received tissue fragments of 2×2 mm subcutaneously at day 0, and tumors were allowed to reach palpable sizes of 118 mm³ (mean) (the study day 8) prior to start the treatments. NOV202 group was administered PO at a dose 30 mg/kg and olaparib group was administered PO at a dose 100 mg/kg. The combination of NOV202 and olaparib group had the same dosage and schedule as in monotherapy. NOV202 was given in the morning (5 ml/kg) and olaparib in the afternoon (10 ml/kg). All three groups were administered 14 days once a day (days 8-22). The tumor volumes and body weights of animals were measured at regular intervals (day 7, 9, 13, 15, 19, 22, 27, all groups, and continued to measure the combination group day 29, 33, 36, 40, 43, 47, 50, 54, 57).

NOV202 inhibited the growth of Ov10584 significantly, resulting in a T/C (tumor/control) value of 37% (stable disease). The combination of NOV202 with olaparib had a distinct synergistic effect. The T/C value was improved to 3% in the combination group, compared to 37% for NOV202 and 20% for olaparib after monotherapy. Tumor remission was almost complete at the end of therapy (mean RTV=0.4, day 22), and continued until day 40 (mean RTV=0.8).

Figure 2:
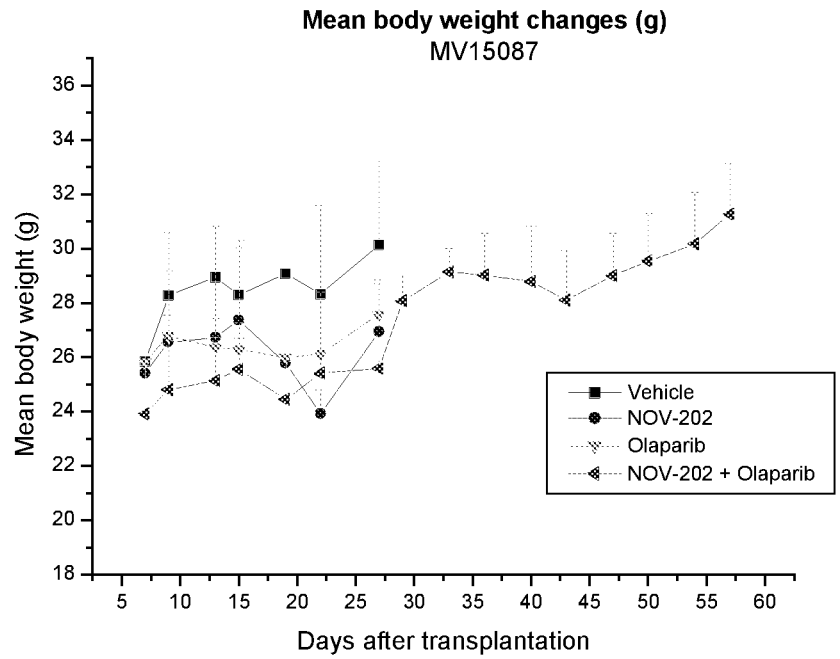
FIG. 2 sets out the mean body weight changes of an in vivo anti-tumor efficacy of NOV202 alone and in combination with olaparib in a patient-derived xenograft of ovarian cancer. Details are provided in Example 1.

Daily treatment with 30 mg/kg NOV202 for 14 days was well tolerated. One day after treatment stop, mice showed 6% body weight loss but they recovered soon. The combination of NOV202 and olaparib was also well tolerated. Results are set out in FIG. 1. The mean body weight changes of the animals are set out in FIG. 2.

EXAMPLE 2

A Study of Anti-Tumor Efficacy of Combination of NOV202 with Olaparib Vs. Combination Plinabulin with Olaparib in a Patient-Derived Xenograft of Ovarian Cancer (Ov0584)

NMRI:nu/nu female (Janvier) mice (8 weeks old) were used as follows: 4 animals in the vehicle group, 4 animals in NOV202 group, olaparib group, plinabulin group, in the combination group of NOV202 and Olaparib, and in the combination group of plinabulin and olaparib, respectively. NOV202 was synthesized as described in WO 2012/127032. Olaparib was purchased from LC Laboratories, and plinabulin was purchased from Sellechem. The patient-derived xenograft Ov10584 was used at passage number 4. All mice received tissue fragments of 2×2 mm subcutaneously into the left flank at day 0, and tumors were allowed to reach palpable sizes of 108 mm³ (mean) (the study day 6) prior to start the treatments. NOV202 group was administered PO at a dose 30 mg/kg and olaparib group was administered PO at a dose 100 mg/kg, and plinabulin was administered i.p. at a dose 7.5 mg/kg. The combination of NOV202 and olaparib group had the same dosage and schedule as in monotherapy, NOV202 was given in the morning (5 ml/kg) and olaparib in the afternoon (10 ml/kg). The combination of plinabulin and olaparib group had also the same dosage and schedule as in monotherapy. NOV202 and olaparib was administered 14 days once a day (days 6-19), and plinabulin was administered days 1, 4, 8, 11, 15 once a day. The tumor volumes and body weights of animals were measured at regular intervals (day 6, 7, 9, 12, 14, 16, 19, 23, 26 and 29), all groups.

NOV202 inhibited the growth of Ov10584 significantly, resulting in a T/C (tumor/control) value of 32% (stable disease). The combination of NOV202 with olaparib had a distinct synergistic effect. The T/C value was improved to 6% in the combination group, compared to 32% for NOV202, 45% for olaparib and 58% for plinabulin after monotherapy. The combination of plinabulin with olaparib had also a synergistic effect. T/C value was improved to 14% in the combination group.

Figure 3:
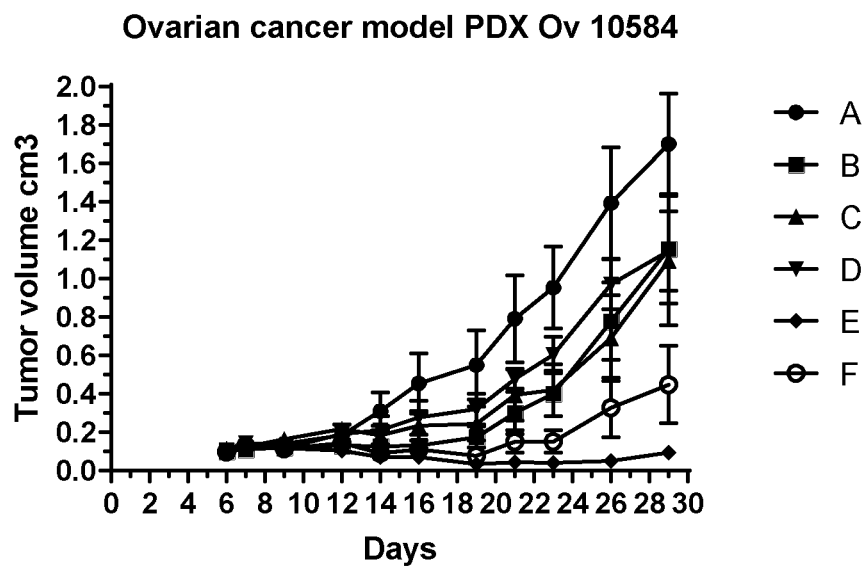
FIG. 3 sets out results of study of an in vivo anti-tumor efficacy of NOV202, olaparib and plinabulin alone, and combination of NOV202 and olaparib, and combination of plinabulin and olaparib, in a patient-derived xenograft of ovarian cancer. Details are provided in Example 2. A represents vehicle, B represents NOV202, C represents olaparib, D represents plinabulin, E represents combination of NOV202 and olaparib, and F represents combination of plinabulin and olaparib. Start of treatments were at day 6 and end of treatment were at day 19 (NOV202 and olaparib) and at day 20 (plinabulin).
Figure 4:
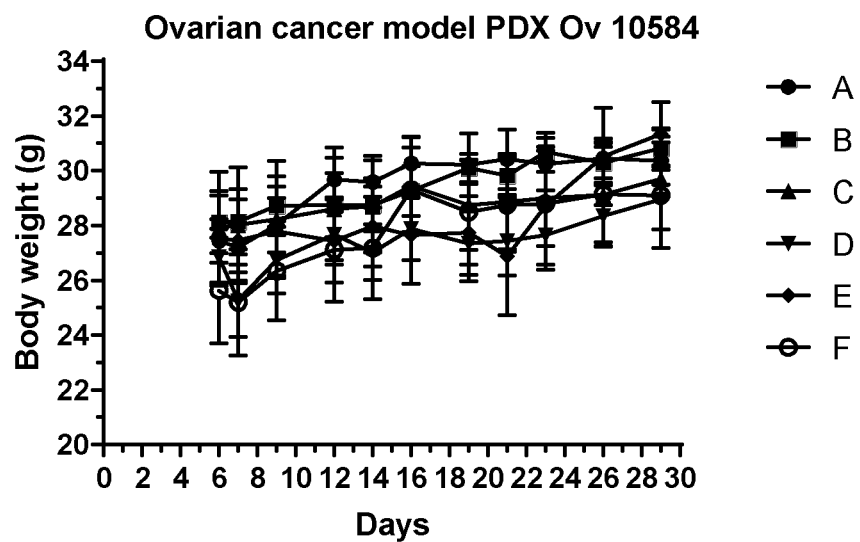
FIG. 4 sets out the mean body weight changes of an in vivo anti-tumor efficacy of NOV202, olaparib and plinabulin alone, and combination of NOV202 and olaparib, and combination of plinabulin and olaparib, in a patient-derived xenograft of ovarian cancer Details are provided in Example 2. A represents vehicle, B represents NOV202, C represents olaparib, D represents plinabulin, E represents combination of NOV202 and olaparib, and F represents combination of plinabulin and olaparib.

Daily treatment for 14 days was well tolerated in all groups. Results are set out in FIG. 3. The mean body weight changes of the animals are set out in FIG. 4. A represents vehicle, B represents NOV202, C represents olaparib, D represents plinabulin, E represents combination of NOV202 and olaparib, and F represents combination of plinabulin and olaparib.

Items of the Invention

1. A method of treating, preventing or alleviating cancer, comprising administering to a subject in need thereof (i) a therapeutically effective amount of a tubulin polymerization inhibitor or a pharmaceutically acceptable salt, hydrate, solvate or amorphous solid thereof, and (ii) a therapeutically effective amount of a poly (ADP-ribose) polymerase (PARP) inhibitor, or a pharmaceutically acceptable salt, hydrate, solvate or amorphous solid thereof.

2. The method of item 1, wherein the tubulin polymerization inhibitor is a compound of formula I, or a pharmaceutically acceptable solvate or salt thereof;
   wherein said formula I is represented by:

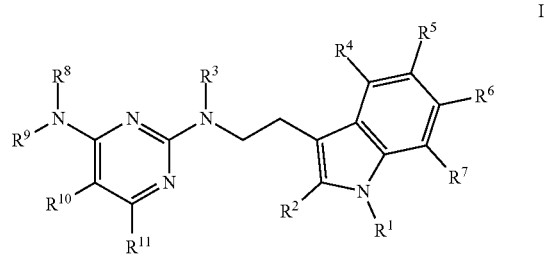

wherein
$R^1$, $R^3$, $R^8$, $R^{12}$, $R^{13}$, and $R^{14}$ represent hydrogen;
$R^2$ represents hydrogen or methyl;
$R^4$, $R^5$, $R^6$, and $R^7$ are independently selected from hydrogen, halogen, hydroxy, $(C_1$-$C_4)$alkyl, $O(C_1$-$C_4)$ alkyl, $O(C_1$-$C_4)$alkyl$(C_2$-$C_5)$heterocyclyl, and $OCF_3$;

$R^{10}$ is selected from hydrogen, $(C_1-C_4)$alkyl and $NH_2$;
$R^{11}$ is selected from hydrogen, $(C_1-C_4)$alkyl, $(CO)NH_2$, and $(C_2-C_5)$heterocyclyl$(C_1-C_4)$alkyl;
$R^9$ is selected from

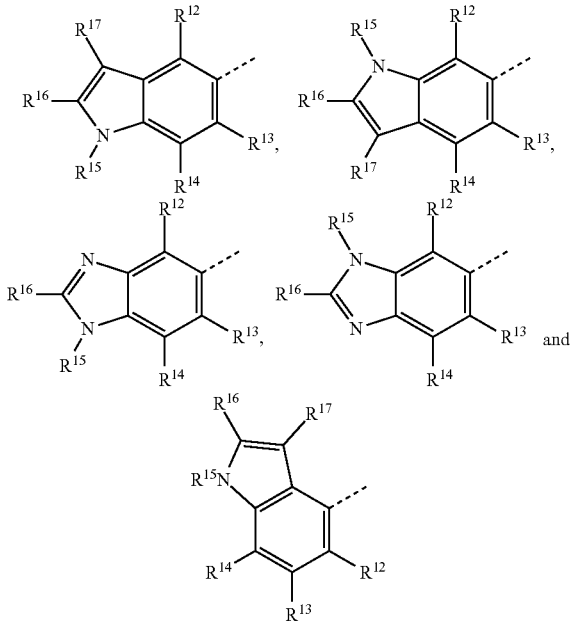

$R^{15}$ is selected from hydrogen and methyl; and
$R^{16}$ and $R^{17}$ are independently selected from hydrogen, $(C_1-C_4)$alkyl, $(C_1-C_4)$alkyl-OH, and (CO)OH.

3. The method of item 2, wherein the tubulin polymerization inhibitor is a compound of formula I which is is selected from:

$N^4$-(1H-indol-5-yl)-$N^2$-[2-(5-methoxy-1H-indol-3-yl)ethyl]pyrimidine-2,4-diamine;
$N^2$-[2-(1H-indol-3-yl)ethyl]-$N^4$-(2-methyl-1H-indol-5-yl)pyrimidine-2,4-diamine;
$N^2$-[2-(5-methoxy-1H-indol-3-yl)ethyl]-$N^4$-(2-methyl-1H-indol-5-yl)pyrimidine-2,4-diamine;
$N^2$-[2-(5-ethoxy-1H-indol-3-yl)ethyl]-$N^4$-(2-methyl-1H-indol-5-yl)pyrimidine-2,4-diamine;
$N^4$-(2-methyl-1H-indol-5-yl)-$N^2$-{2-[5-(trifluoromethoxy)-1H-indol-3-yl]ethyl}pyrimidine-2,4-diamine;
$N^2$-[2-(5-methyl-1H-indol-3-yl)ethyl]-$N^4$-(2-methyl-1H-indol-5-yl)pyrimidine-2,4-diamine;
$N^2$-[2-(5-fluoro-1H-indol-3-yl)ethyl]-$N^4$-(2-methyl-1H-indol-5-yl)pyrimidine-2,4-diamine;
$N^2$-[2-(6-methoxy-1H-indol-3-yl)ethyl]-$N^4$-(2-methyl-1H-indol-5-yl)pyrimidine-2,4-diamine;
$N^2$-[2-(7-methoxy-1H-indol-3-yl)ethyl]-$N^4$-(2-methyl-1H-indol-5-yl)pyrimidine-2,4-diamine;
$N^4$-(1,2-dimethyl-1H-indol-5-yl)-$N^2$-[2-(5-methoxy-1H-indol-3-yl)ethyl]pyrimidine-2,4-diamine;
$N^4$-(2,3-dimethyl-1H-indol-5-yl)-$N^2$-[2-(5-methoxy-1H-indol-3-yl)ethyl]pyrimidine-2,4-diamine;
(5-{2-[2-(5-methoxy-1H-indol-3-yl)ethylamino]pyrimidin-4-ylamino}-1H-indol-2-yl)methanol;
methyl 5-{2-[2-(5-methoxy-1H-indol-3-yl)ethylamino]pyrimidin-4-ylamino}-1H-indole-2-carboxylate;
$N^4$-(1H-benzo[d]imidazol-5-yl)-$N^2$-[2-(5-methoxy-1H-indol-3-yl)ethyl]pyrimidine-2,4-diamine;
$N^2$-[2-(5-methoxy-1H-indol-3-yl)ethyl]-$N^4$-(2-methyl-1H-benzo[d]imidazol-5-yl)pyrimidine-2,4-diamine;
$N^4$-(1H-indol-6-yl)-$N^2$-[2-(5-methoxy-1H-indol-3-yl)ethyl]pyrimidine-2,4-diamine;
$N^4$-(1H-indol-4-yl)-$N^2$-[2-(5-methoxy-1H-indol-3-yl)ethyl]pyrimidine-2,4-diamine;
$N^2$-[2-(1H-indol-3-yl)ethyl]-6-methyl-$N^4$-(2-methyl-1H-indol-5-yl)pyrimidine-2,4-diamine;
$N^2$-[2-(5-methoxy-1H-indol-3-yl)ethyl]-6-methyl-$N^4$-(2-methyl-1H-indol-5-yl)pyrimidine-2,4-diamine;
2-[2-(5-methoxy-1H-indol-3-yl)ethylamino]-6-(2-methyl-1H-indol-5-ylamino)pyrimidine-4-carboxamide; and
$N^2$-[2-(5-methoxy-1H-indol-3-yl)ethyl]-5-methyl-$N^4$-(2-methyl-1H-indol-5-yl)pyrimidine-2,4-diamine;
$N^2$-[2-(4-methoxy-1H-indol-3-yl)ethyl]-$N^4$-(2-methyl-1H-indol-5-yl)pyrimidine-2,4-diamine;
$N^4$-(2-methyl-1H-indol-5-yl)-$N^2$-[2-(5-propoxy-1H-indol-3-yl)ethyl]pyrimidine-2,4-diamine;
$N^2$-[2-(5-isopropoxy-1H-indol-3-yl)ethyl]-$N^4$-(2-methyl-1H-indol-5-yl)pyrimidine-2,4-diamine;
$N^2$-[2-(5,6-dimethoxy-1H-indol-3-yl)ethyl]-$N^4$-(2-methyl-1H-indol-5-yl)pyrimidine-2,4-diamine;
$N^2$-[2-(5-methoxy-7-methyl-1H-indol-3-yl)ethyl]-$N^4$-(2-methyl-1H-indol-5-yl)pyrimidine-2,4-diamine;
$N^2$-[2-(5-methoxy-1H-indol-3-yl)ethyl]-$N^4$-(1-methyl-1H-benzo[d]imidazol-5-yl)pyrimidine-2,4-diamine;
$N^4$-(1,2-dimethyl-1H-benzo[d]imidazol-5-yl)-$N^2$-[2-(5-methoxy-1H-indol-3-yl)ethyl]pyrimidine-2,4-diamine;
$N^2$-[2-(5-methoxy-1H-indol-3-yl)ethyl]-$N^4$-(1-methyl-1H-indol-4-yl)pyrimidine-2,4-diamine;
$N^2$-[2-(5-ethoxy-1H-indol-3-yl)ethyl]-6-methyl-$N^4$-(2-methyl-1H-indol-5-yl)pyrimidine-2,4-diamine;
$N^2$-[2-(5-methoxy-2-methyl-1H-indol-3-yl)ethyl]-6-methyl-$N^4$-(2-methyl-1H-indol-5-yl)pyrimidine-2,4-diamine;
$N^2$-[2-(5-methoxy-1H-indol-3-yl)ethyl]-6-methyl-$N^4$-(2-methyl-1H-benzo[d]imidazol-5-yl)pyrimidine-2,4-diamine;
$N^2$-[2-(5-ethoxy-1H-indol-3-yl)ethyl]-6-methyl-$N^4$-(2-methyl-1H-benzo[d]imidazol-5-yl)pyrimidine-2,4-diamine;
[5-(2-{[2-(5-methoxy-1H-indol-3-yl)ethyl][methyl]amino}pyrimidin-4-ylamino)-1H-indol-2-yl]methanol;
(5-{2-[2-(5-methoxy-1H-indol-3-yl)ethylamino]pyrimidin-4-ylamino}-1-methyl-1H-benzo[d]imidazol-2-yl)methanol;
$N^2$-[2-(5-methoxy-1H-indol-3-yl)ethyl]-$N^4$-methyl-$N^4$-(2-methyl-1H-indol-5-yl)pyrimidine-2,4-diamine;
$N^4$-(1,2-dimethyl-1H-indol-5-yl)-$N^2$-[2-(5-methoxy-1H-indol-3-yl)ethyl]-$N^4$-methylpyrimidine-2,4-diamine;
[5-({2-[2-(5-ethoxy-1H-indol-3-yl)ethylamino]pyrimidin-4-yl}amino)-1H-indol-2-yl]methanol;
$N^2$-[2-(5-methoxy-1H-indol-3-yl)ethyl]-$N^4$-(2-methyl-1H-indol-6-yl)pyrimidine-2,4-diamine;
$N^2$-[2-(5-ethoxy-1H-indol-3-yl)ethyl]-$N^4$-(2-methyl-1H-indol-6-yl)pyrimidine-2,4-diamine;
$N^2$-[2-(5-methoxy-1H-indol-3-yl)ethyl]-$N^4$-(1-methylindol-6-yl)pyrimidine-2,4-diamine;
$N^2$-[2-(5-ethoxy-1H-indol-3-yl)ethyl]-$N^4$-(1-methylindol-6-yl)pyrimidine-2,4-diamine;
$N^2$-[2-(5-methoxy-1H-indol-3-yl)ethyl]-$N^4$-(2-methyl-1H-indol-4-yl)pyrimidine-2,4-diamine;
$N^2$-[2-(5-ethoxy-1H-indol-3-yl)ethyl]-$N^4$-(2-methyl-1H-indol-4-yl)pyrimidine-2,4-diamine;
3-[2-({4-[(1-methylindol-4-yl)amino]pyrimidin-2-yl}amino)ethyl]-1H-indol-5-ol;
$N^2$-[2-(5-ethoxy-1H-indol-3-yl)ethyl]-$N^4$-(1-methylindol-4-yl)pyrimidine-2,4-diamine;

N⁴-(1,2-dimethylindol-4-yl)-N²-[2-(5-methoxy-1H-indol-3-yl)ethyl]pyrimidine-2,4-diamine;
N²-[2-(5-methoxy-1H-indol-3-yl)ethyl]-N⁴-(2-methyl-1H-benzimidazol-4-yl)pyrimidine-2,4-diamine;
N²-[2-(5-ethoxy-1H-indol-3-yl)ethyl]-N⁴-(2-methyl-1H-benzimidazol-4-yl)pyrimidine-2,4-diamine;
2-[2-(5-ethoxy-1H-indol-3-yl)ethylamino]-6-[(2-methyl-1H-indol-5-yl)amino]pyrimidine-4-carboxamide;
6-[(1,2-dimethylbenzimidazol-5-yl)amino]-2-[2-(5-methoxy-1H-indol-3-yl)ethylamino]pyrimidine-4-carboxamide;
2-[2-(5-methoxy-1H-indol-3-yl)ethylamino]-6-[(1-methyl-indol-4-yl)amino]pyrimidine-4-carboxamide;
2-[2-(5-ethoxy-1H-indol-3-yl)ethylamino]-6-[(1-methylindol-4-yl)amino]pyrimidine-4-carboxamide;
N²-[2-(5-methoxy-1H-indol-3-yl)ethyl]-N⁴-(1-methylindol-4-yl)-6-(4-methylpiperazin-1-yl)pyrimidine-2,4-diamine; and
N²-[2-(5-ethoxy-1H-indol-3-yl)ethyl]-N⁴-(2-methyl-1H-indol-5-yl)pyrimidine-2,4,5-triamine.

4. The method of item 1, wherein the tubulin polymerization inhibitor is a I compound of formula I which is N²-[2-(5-methoxy-1H-indol-3-yl)ethyl]-N⁴-(1-methyl-1H-indol-4-yl)pyrimidine-2,4-diamine (NOV202).

5. The method of item 1, wherein the tubulin polymerization inhibitor is selected from combretastatin CA-4P (zybrestat), AVE-8062 (ombrabulin), BNC105P, MPC-6827 (azixa), ZD6126 (ANG453), Oxi-4503, BPI-2358 (plinabulin), MN029 (denibulin), EPC-2407 (crinobulin), ZIO-301 (indibulin), T115, BPROL075 and ABT-751. 6. The method of item 1, wherein the tubulin polymerization inhibitor is the compound (plinabulin):

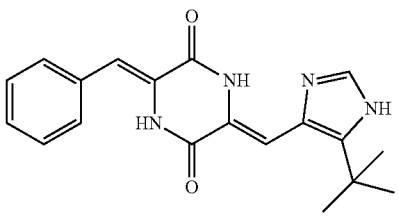 [SMILES: CC(C)(C)c1[nH]cnc1/C=c1\[nH]c(=O)/c(=C/c2ccccc2)[nH]c1=O]

or a pharmaceutically acceptable solvate or salt thereof.

7. The method according to any one of items 1 to 6, wherein said poly (ADP-ribose) polymerase (PARP) inhibitor is selected from olaparib, niraparib, veliparib, talazoparib, rucaparib, iniparib, fluzoparib, AZD2461, UPF 1069, PJ34, A-966492, AG-14361, E7449 and NMS-P118.

8. The method according to any one of items 1 to 6, wherein said poly (ADP-ribose) polymerase (PARP) inhibitor is olaparib.

9. The method according to any one of items 1 to 8, wherein said subject is a human patient.

10. The method according to any one of items 1 to 9, wherein said subject is diagnosed with a cancer, in treatment for cancer, or in post-therapy recovery from cancer.

11. The method according to any one of items 1 to 10, wherein said cancer is a primary tumor.

12. The method according to any one of items 1 to 10, wherein said cancer is a metastasis.

13. The method according to any one of items 1 to 10, wherein said cancer is a solid tumor.

14. The method according to any one of items 1 to 10, wherein said cancer is a BRCA mutated tumor.

15. The method to any one of items 1 to 10, wherein said cancer is a BRCA mutated breast, ovarian, prostate or pancreas cancer.

16. The method to any one of items 1 to 10, wherein said cancer is a p53 suppressor gene mutated tumor.

17. The method to any one of items 1 to 10, wherein said cancer is a p53 mutated breast, ovarian, prostate, lung, brain or pancreas cancer.

18. The method to any one of items 1 to 10, wherein said cancer is a p53 missense mutated tumor with expression of the full-length mutant p53 protein.

19. The method to any one of items 1 to 10, wherein said cancer is a p53 missense mutated breast, ovarian, prostate, lung, brain or pancreas cancer with expression of the full-length mutant p53 protein.

20. The method to any one of items 1 to 10, wherein said cancer is a homologous recombination repair defect tumor with mutations in repair genes other than BRCA1/BRCA2.

21. The method to any one of items 1 to 10, wherein said cancer is a homologous recombination repair defect breast, ovarian, prostate, lung, brain or pancreas cancer with mutations in repair genes other than BRCA1/BRCA2.

22. The method to any one of items 1 to 10, wherein said cancer is a homologous recombination repair defect tumor with mutations in repair genes other than BRCA1/BRCA2, such as ATM, ATR, PALB2, RAD51, CHEK1 and CHEK2, as well as epigenetic loss of BRCA1 function through promoter methylation.

23. The method to any one of items 1 to 10, wherein said cancer is a homologous recombination repair defect breast, ovarian, prostate, lung, brain or pancreas cancer with mutations in repair genes other than BRCA1/BRCA2, such as ATM, ATR, PALB2, RAD51, CHEK1 and CHEK2, as well as epigenetic loss of BRCA1 function through promoter methylation.

24. The method according to any one of items 1 to 10, wherein said cancer is selected from the group consisting of breast cancer, lung cancer, ovarian cancer, endometrial cancer, prostate cancer, pharyngeal cancer, esophageal cancer, glioblastoma, adrenal cancer, B-cell malignancies, biliary tract cancer, bladder cancer, bone cancer, brain cancer, cervical cancer, choriocarcinoma, colon cancer, colorectal cancer, connective tissue cancer, cancer of the digestive system, gallbladder cancer, gastric cancer, cancer of the head and neck, hepatocellular carcinoma, intra-epithelial neoplasm, kidney cancer, liver cancer, lymphoma, skin cancer, neuroblastoma, mesothelioma, neuroglioma, oral cavity cancer, pediatric cancer, pancreatic cancer, pancreatic endocrine tumors, pituitary adenoma, thymoma, renal cell carcinoma, cancer of the respiratory system, salivary gland cancer, sarcoma, small bowel cancer, testicular cancer, thyroid cancer, ureteral cancer, cancer of the urinary system, and hematological cancer.

25. The method according to item 24, wherein said cancer is ovarian cancer.

26. The method according to item 24, wherein said cancer is BRCA mutated ovarian cancer.

27. The method according to item 24, wherein said breast cancer is selected from estrogen receptor positive or negative, progesterone receptor positive or negative, HER-2 positive or negative, triple-negative breast cancer, or BRCA1 and/or BRCA2 positive or negative breast cancer.

28. The method according to item 24, wherein said lung cancer is selected from non-small cell lung cancer and small cell lung cancer.
29. The method according to item 24, wherein said skin cancer is selected from melanoma and basal cell carcinoma.
30. The method according to item 24, wherein said sarcoma is selected from Ewing's sarcoma, fibrosarcoma, and rhabdomyosarcoma.
31. The method according to item 24, wherein said hematological cancer is selected from leukemia, lymphoma and multiple myeloma.
32. The method according to any one of items 1 to 31, wherein said poly (ADP-ribose) polymerase (PARP) inhibitor is administered at a dose ranging from 0.5 to 100 mg/kg per day.
33. The method according to any one of items 1 to 32, wherein said tubulin polymerization inhibitor and/or said poly (ADP-ribose) polymerase (PARP) inhibitor is administered by intravenous infusion.
34. The method according to any one of items 1 to 32, wherein said tubulin polymerization inhibitor and/or said poly (ADP-ribose) polymerase (PARP) inhibitor is administered orally.
35. The method according to any one of items 1 to 34, wherein said tubulin polymerization inhibitor and said poly (ADP-ribose) polymerase (PARP) inhibitor is administered once daily, during a 14-day cycle.
36. The method according to any one of item 1 to 35, wherein said tubulin polymerization inhibitor is administered at a dose ranging from 0.5 to 50 mg/kg per day.
37. The method according to item 36, wherein said tubulin polymerization inhibitor is a compound of formula I.
38. The method according to any one of item 1 to 4 and 7 to 37, wherein the tubulin polymerization inhibitor is a compound of formula I which is $N^2$-[2-(5-methoxy-1H-indol-3-yl)ethyl]-$N^4$-(1-methyl-1H-indol-4-yl)pyrimidine-2,4-diamine (NOV202); said poly (ADP-ribose) polymerase (PARP) inhibitor is olaparib; and said cancer is ovarian cancer.
39. The method of item 1, wherein the tubulin polymerization inhibitor is plinabulin or a pharmaceutically acceptable salt, hydrate, solvate or amorphous solid thereof, the PARP inhibitor is olaparib or a pharmaceutically acceptable solvate or salt thereof.
40. The method according to item 39, wherein said cancer is as defined in any one of items 11 to 31.
41. A compound of formula I, or a pharmaceutically acceptable solvate or salt thereof, and a poly (ADP-ribose) polymerase (PARP) inhibitor, or a pharmaceutically acceptable salt, hydrate, solvate or amorphous solid thereof, in combination, for use in treatment of cancer; wherein said formula I is represented by:

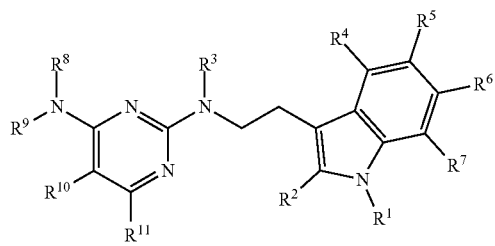

I wherein
$R^1$, $R^3$, $R^8$, $R^{12}$, $R^{13}$, and $R^{14}$ represent hydrogen;
$R^2$ represents hydrogen or methyl;

$R^4$, $R^5$, $R^6$, and $R^7$ are independently selected from hydrogen, halogen, hydroxy, $(C_1-C_4)$alkyl, $O(C_1-C_4)$alkyl, $O(C_1-C_4)$alkyl$(C_2-C_5)$heterocyclyl, and $OCF_3$;
$R^{10}$ is selected from hydrogen, $(C_1-C_4)$alkyl and $NH_2$;
$R^{11}$ is selected from hydrogen, $(C_1-C_4)$alkyl, $(CO)NH_2$, and $(C_2-C_5)$heterocyclyl$(C_1-C_4)$alkyl;
$R^9$ is selected from

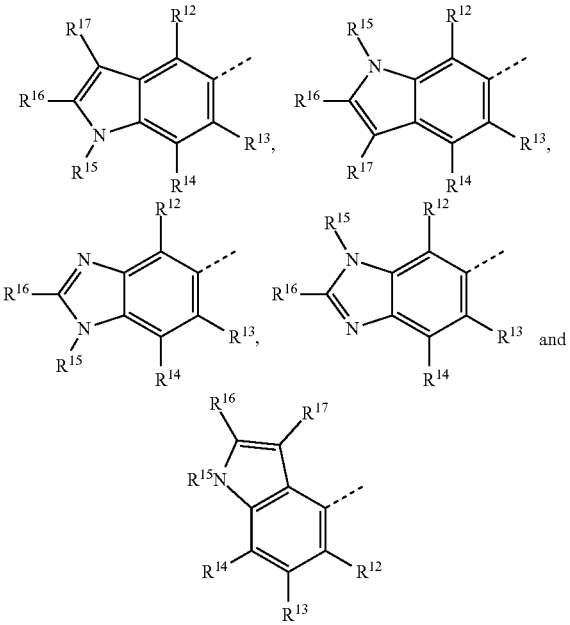

$R^{15}$ is selected from hydrogen and methyl; and
$R^{16}$ and $R^{17}$ are independently selected from hydrogen, $(C_1-C_4)$alkyl, $(C_1-C_4)$alkyl-OH, and $(CO)OH$.
38. The combination for use according to item 37, wherein said compound of formula I is selected from:
$N^4$-(1H-indol-5-yl)-$N^2$-[2-(5-methoxy-1H-indol-3-yl)ethyl]pyrimidine-2,4-diamine;
$N^2$-[2-(1H-indol-3-yl)ethyl]-$N^4$-(2-methyl-1H-indol-5-yl)pyrimidine-2,4-diamine;
$N^2$-[2-(5-methoxy-1H-indol-3-yl)ethyl]-$N^4$-(2-methyl-1H-indol-5-yl)pyrimidine-2,4-diamine;
$N^2$-[2-(5-ethoxy-1H-indol-3-yl)ethyl]-$N^4$-(2-methyl-1H-indol-5-yl)pyrimidine-2,4-diamine;
$N^4$-(2-methyl-1H-indol-5-yl)-$N^2$-{2-[5-(trifluoromethoxy)-1H-indol-3-yl]ethyl}pyrimidine-2,4-diamine;
$N^2$-[2-(5-methyl-1H-indol-3-yl)ethyl]-$N^4$-(2-methyl-1H-indol-5-yl)pyrimidine-2,4-diamine;
$N^2$-[2-(5-fluoro-1H-indol-3-yl)ethyl]-$N^4$-(2-methyl-1H-indol-5-yl)pyrimidine-2,4-diamine;
$N^2$-[2-(6-methoxy-1H-indol-3-yl)ethyl]-$N^4$-(2-methyl-1H-indol-5-yl)pyrimidine-2,4-diamine;
$N^2$-[2-(7-methoxy-1H-indol-3-yl)ethyl]-$N^4$-(2-methyl-1H-indol-5-yl)pyrimidine-2,4-diamine;
$N^4$-(1,2-dimethyl-1H-indol-5-yl)-$N^2$-[2-(5-methoxy-1H-indol-3-yl)ethyl]pyrimidine-2,4-diamine;
$N^4$-(2,3-dimethyl-1H-indol-5-yl)-$N^2$-[2-(5-methoxy-1H-indol-3-yl)ethyl]pyrimidine-2,4-diamine;
(5-{2-[2-(5-methoxy-1H-indol-3-yl)ethylamino]pyrimidin-4-ylamino}-1H-indol-2-yl)methanol; methyl 5-{2-[2-(5-methoxy-1H-indol-3-yl)ethylamino]pyrimidin-4-ylamino}-1H-indole-2-carboxylate;
$N^4$-(1H-benzo[d]imidazol-5-yl)-$N^2$-[2-(5-methoxy-1H-indol-3-yl)ethyl]pyrimidine-2,4-diamine;

N²-[2-(5-methoxy-1H-indol-3-yl)ethyl]-N⁴-(2-methyl-1H-benzo[d]imidazol-5-yl)pyrimidine-2,4-diamine;
N⁴-(1H-indol-6-yl)-N²-[2-(5-methoxy-1H-indol-3-yl)ethyl]pyrimidine-2,4-diamine;
N⁴-(1H-indol-4-yl)-N²-[2-(5-methoxy-1H-indol-3-yl)ethyl]pyrimidine-2,4-diamine;
N²-[2-(1H-indol-3-yl)ethyl]-6-methyl-N⁴-(2-methyl-1H-indol-5-yl)pyrimidine-2,4-diamine;
N²-[2-(5-methoxy-1H-indol-3-yl)ethyl]-6-methyl-N⁴-(2-methyl-1H-indol-5-yl)pyrimidine-2,4-diamine;
2-[2-(5-methoxy-1H-indol-3-yl)ethylamino]-6-(2-methyl-1H-indol-5-ylamino)pyrimidine-4-carboxamide; and
N²-[2-(5-methoxy-1H-indol-3-yl)ethyl]-5-methyl-N⁴-(2-methyl-1H-indol-5-yl)pyrimidine-2,4-diamine;
N²-[2-(4-methoxy-1H-indol-3-yl)ethyl]-N⁴-(2-methyl-1H-indol-5-yl)pyrimidine-2,4-diamine;
N⁴-(2-methyl-1H-indol-5-yl)-N²-[2-(5-propoxy-1H-indol-3-yl)ethyl]pyrimidine-2,4-diamine;
N²-[2-(5-isopropoxy-1H-indol-3-yl)ethyl]-N⁴-(2-methyl-1H-indol-5-yl)pyrimidine-2,4-diamine;
N²-[2-(5,6-dimethoxy-1H-indol-3-yl)ethyl]-N⁴-(2-methyl-1H-indol-5-yl)pyrimidine-2,4-diamine;
N²-[2-(5-methoxy-7-methyl-1H-indol-3-yl)ethyl]-N⁴-(2-methyl-1H-indol-5-yl)pyrimidine-2,4-diamine;
N²-[2-(5-methoxy-1H-indol-3-yl)ethyl]-N⁴-(1-methyl-1H-benzo[d]imidazol-5-yl)pyrimidine-2,4-diamine;
N⁴-(1,2-dimethyl-1H-benzo[d]imidazol-5-yl)-N²-[2-(5-methoxy-1H-indol-3-yl)ethyl]pyrimidine-2,4-diamine;
N²-[2-(5-methoxy-1H-indol-3-yl)ethyl]-N⁴-(1-methyl-1H-indol-4-yl)pyrimidine-2,4-diamine;
N²-[2-(5-ethoxy-1H-indol-3-yl)ethyl]-6-methyl-N⁴-(2-methyl-1H-indol-5-yl)pyrimidine-2,4-diamine;
N²-[2-(5-methoxy-2-methyl-1H-indol-3-yl)ethyl]-6-methyl-N⁴-(2-methyl-1H-indol-5-yl)pyrimidine-2,4-diamine;
N²-[2-(5-methoxy-1H-indol-3-yl)ethyl]-6-methyl-N⁴-(2-methyl-1H-benzo[d]imidazol-5-yl)pyrimidine-2,4-diamine;
N²-[2-(5-ethoxy-1H-indol-3-yl)ethyl]-6-methyl-N⁴-(2-methyl-1H-benzo[d]imidazol-5-yl)pyrimidine-2,4-diamine;
[5-(2-{[2-(5-methoxy-1H-indol-3-yl)ethyl][methyl]amino}pyrimidin-4-ylamino)-1H-indol-2-yl]methanol;
(5-{2-[2-(5-methoxy-1H-indol-3-yl)ethylamino]pyrimidin-4-ylamino}-1-methyl-1H-benzo[d]imidazol-2-yl)methanol;
N²-[2-(5-methoxy-1H-indol-3-yl)ethyl]-N⁴-methyl-N⁴-(2-methyl-1H-indol-5-yl)pyrimidine-2,4-diamine;
N⁴-(1,2-dimethyl-1H-indol-5-yl)-N²-[2-(5-methoxy-1H-indol-3-yl)ethyl]-N⁴-methylpyrimidine-2,4-diamine;
[5-({2-[2-(5-ethoxy-1H-indol-3-yl)ethylamino]pyrimidin-4-yl}amino)-1H-indol-2-yl]methanol;
N²-[2-(5-methoxy-1H-indol-3-yl)ethyl]-N⁴-(2-methyl-1H-indol-6-yl)pyrimidine-2,4-diamine;
N²-[2-(5-ethoxy-1H-indol-3-yl)ethyl]-N⁴-(2-methyl-1H-indol-6-yl)pyrimidine-2,4-diamine;
N²-[2-(5-methoxy-1H-indol-3-yl)ethyl]-N⁴-(1-methylindol-6-yl)pyrimidine-2,4-diamine;
N²-[2-(5-ethoxy-1H-indol-3-yl)ethyl]-N⁴-(1-methylindol-6-yl)pyrimidine-2,4-diamine;
N²-[2-(5-methoxy-1H-indol-3-yl)ethyl]-N⁴-(2-methyl-1H-indol-4-yl)pyrimidine-2,4-diamine;
N²-[2-(5-ethoxy-1H-indol-3-yl)ethyl]-N⁴-(2-methyl-1H-indol-4-yl)pyrimidine-2,4-diamine;
3-[2-({4-[(1-methylindol-4-yl)amino]pyrimidin-2-yl}amino)ethyl]-1H-indol-5-ol;
N²-[2-(5-ethoxy-1H-indol-3-yl)ethyl]-N⁴-(1-methylindol-4-yl)pyrimidine-2,4-diamine;
N⁴-(1,2-dimethylindol-4-yl)-N²-[2-(5-methoxy-1H-indol-3-yl)ethyl]pyrimidine-2,4-diamine;
N²-[2-(5-methoxy-1H-indol-3-yl)ethyl]-N⁴-(2-methyl-1H-benzimidazol-4-yl)pyrimidine-2,4-diamine;
N²-[2-(5-ethoxy-1H-indol-3-yl)ethyl]-N⁴-(2-methyl-1H-benzimidazol-4-yl)pyrimidine-2,4-diamine;
2-[2-(5-ethoxy-1H-indol-3-yl)ethylamino]-6-[(2-methyl-1H-indol-5-yl)amino]pyrimidine-4-carboxamide;
6-[(1,2-dimethylbenzimidazol-5-yl)amino]-2-[2-(5-methoxy-1H-indol-3-yl)ethylamino]pyrimidine-4-carboxamide;
2-[2-(5-methoxy-1H-indol-3-yl)ethylamino]-6-[(1-methylindol-4-yl)amino]pyrimidine-4-carboxamide;
2-[2-(5-ethoxy-1H-indol-3-yl)ethylamino]-6-[(1-methylindol-4-yl)amino]pyrimidine-4-carboxamide;
N²-[2-(5-methoxy-1H-indol-3-yl)ethyl]-N⁴-(1-methylindol-4-yl)-6-(4-methylpiperazin-1-yl)pyrimidine-2,4-diamine; and
N²-[2-(5-ethoxy-1H-indol-3-yl)ethyl]-N⁴-(2-methyl-1H-indol-5-yl)pyrimidine-2,4,5-triamine.

42. The combination for use according to item 41, wherein said compound of formula I is N²-[2-(5-methoxy-1H-indol-3-yl)ethyl]-N⁴-(1-methyl-1H-indol-4-yl)pyrimidine-2,4-diamine (NOV202).

43. The combination for use according to any one of items 41 to 42, wherein said poly (ADP-ribose) polymerase (PARP) inhibitor is selected from olaparib, niraparib, veliparib, talazoparib, rucaparib, iniparib, fluzoparib, AZD2461, UPF 1069, PJ34, A-966492, AG-14361, E7449 and NMS-P118.

44. The combination for use according to any one of items 41 to 43, wherein said poly (ADP-ribose) polymerase (PARP) inhibitor is olaparib.

45. The combination for use according to any one of items 41 to 44, wherein said cancer is a primary tumor.

46. The combination for use according to any one of items 41 to 44, wherein said cancer is a metastasis.

47. The combination for use according to any one of items 41 to 44, wherein said cancer is a solid tumor.

48. The combination for use according to any one of items 41 to 44, wherein said cancer is a BRCA mutated tumor.

49. The combination for use according to any one of items 41 to 44, wherein said cancer is a BRCA mutated breast, ovarian, prostate or pancreas cancer.

50. The combination for use according to any one of items 41 to 44, wherein said cancer is a p53 suppressor gene mutated tumor.

51. The combination for use according to any one of items 41 to 44, wherein said cancer is a p53 mutated breast, ovarian, prostate, lung, brain or pancreas cancer.

52. The combination for use according to any one of items 41 to 44, wherein said cancer is a p53 missense mutated tumor with expression of the full-length mutant p53 protein.

53. The combination for use according to any one of items 41 to 44, wherein said cancer is a p53 missense mutated breast, ovarian, prostate, lung, brain or pancreas cancer with expression of the full-length mutant p53 protein.

54. The combination for use according to any one of items 41 to 44, wherein said cancer is a homologous recombination repair defect tumor with mutations in repair genes other than BRCA1/BRCA2.

55. The combination for use according to any one of items 41 to 44, wherein said cancer is a homologous recombination repair defect breast, ovarian, prostate, lung, brain or pancreas cancer with mutations in repair genes other than BRCA1/BRCA2.
56. The combination for use according to any one of items 41 to 44, wherein said cancer is a homologous recombination repair defect tumor with mutations in repair genes other than BRCA1/BRCA2, such as ATM, ATR, PALB2, RAD51, CHEK1 and CHEK2, as well as epigenetic loss of BRCA1 function through promoter methylation.
57. The combination for use according to any one of items 41 to 44, wherein said cancer is a homologous recombination repair defect breast, ovarian, prostate, lung, brain or pancreas cancer with mutations in repair genes other than BRCA1/BRCA2, such as ATM, ATR, PALB2, RAD51, CHEK1 and CHEK2, as well as epigenetic loss of BRCA1 function through promoter methylation.
58. The combination for use according to any one of items 41 to 44, wherein said cancer is selected from the group consisting of breast cancer, lung cancer, ovarian cancer, endometrial cancer, prostate cancer, pharyngeal cancer, esophageal cancer, glioblastoma, adrenal cancer, B-cell malignancies, biliary tract cancer, bladder cancer, bone cancer, brain cancer, cervical cancer, choriocarcinoma, colon cancer, colorectal cancer, connective tissue cancer, cancer of the digestive system, gallbladder cancer, gastric cancer, cancer of the head and neck, hepatocellular carcinoma, intra-epithelial neoplasm, kidney cancer, liver cancer, lymphoma, skin cancer, neuroblastoma, mesothelioma, neuroglioma, oral cavity cancer, pediatric cancer, pancreatic cancer, pancreatic endocrine tumors, pituitary adenoma, thymoma, renal cell carcinoma, cancer of the respiratory system, salivary gland cancer, sarcoma, small bowel cancer, testicular cancer, thyroid cancer, ureteral cancer, cancer of the urinary system, and hematological cancer.
59. The combination for use according to item 58, wherein said cancer is ovarian cancer.
60. The combination for use according to item 59, wherein said ovarian cancer is BRCA mutated ovarian cancer.
61. The combination for use according to item 58, wherein said breast cancer is selected from estrogen receptor positive or negative, progesterone receptor positive or negative, HER-2 positive or negative, triple-negative breast cancer, or BRCA1 and/or BRCA2 positive or negative breast cancer.
62. The combination for use according to item 58, wherein said lung cancer is selected from non-small cell lung cancer and small cell lung cancer.
63. The combination for use according to item 58, wherein said skin cancer is selected from melanoma and basal cell carcinoma.
64. The combination for use according to item 58, wherein said sarcoma is selected from Ewing's sarcoma, fibrosarcoma, and rhabdomyosarcoma.
65. The combination for use according to item 58, wherein said hematological cancer is selected from leukemia, lymphoma and multiple myeloma.
66. The combination for use according to any one of items 41 to 65, wherein said compound of formula I is $N^2$-[2-(5-methoxy-1H-indol-3-yl)ethyl]-$N^4$-(1-methyl-1H-indol-4-yl)pyrimidine-2,4-diamine (NOV202); said poly (ADP-ribose) polymerase (PARP) inhibitor is olaparib; and said cancer is ovarian cancer.
67. The combination for use according to any one of items 41 to 66, wherein said compound of formula I is administered at a dose ranging from 0.5 to 50 mg/kg per day.
68. The combination for use according to any one of items 41 to 66, wherein said poly (ADP-ribose) polymerase (PARP) inhibitor is administered at a dose ranging from 0.5 to 100 mg/kg per day.
69. The combination for use according to any one of items 41 to 68, wherein said compound of formula I and/or said poly (ADP-ribose) polymerase (PARP) inhibitor is administered by intravenous infusion.
70. The combination for use according to any one of items 41 to 68, wherein said compound of formula I and/or said poly (ADP-ribose) polymerase (PARP) inhibitor is administered orally.
71. The combination for use according to any one of items 41 to 70, wherein said compound of formula I and said poly (ADP-ribose) polymerase (PARP) inhibitor is administered once daily, during a 14-day cycle.
72. A pharmaceutical composition for use in treatment of ovarian cancer, comprising NOV202 and/or a pharmaceutically acceptable salt thereof, and olaparib and/or a pharmaceutically acceptable salt thereof.
73. A kit for use in treating cancer or decreasing tumor size, said kit comprising (i) a compound of formula I or a pharmaceutically acceptable solvate or salt thereof, according to item 1 or item 36; and (ii) a poly (ADP-ribose) polymerase (PARP) inhibitor, or a and/or a pharmaceutically acceptable salt, hydrate, solvate or amorphous solid thereof.
74. The kit for use, according to item 73, wherein said compound of formula I is $N^2$-[2-(5-methoxy-1H-indol-3-yl)ethyl]-$N^4$-(1-methyl-1H-indol-4-yl)pyrimidine-2,4-diamine (NOV202); said poly (ADP-ribose) polymerase (PARP) inhibitor is olaparib; and said cancer is ovarian cancer.
75. Olaparib, or a pharmaceutically acceptable solvate or salt thereof, and plinabulin, or a pharmaceutically acceptable salt, hydrate, solvate or amorphous solid thereof, in combination, for use in treatment of cancer.
76. The combination for use, according to item 72, wherein said cancer is as defined in any one of items 45 to 65.
77. A tubulin polymerization inhibitor, or a pharmaceutically acceptable solvate or salt thereof, and a poly (ADP-ribose) polymerase (PARP) inhibitor, or a pharmaceutically acceptable salt, hydrate, solvate or amorphous solid thereof, in combination, for use in treatment of cancer.
78. The combination for use of item 77, wherein the tubulin polymerization inhibitor is combretastatin CA-4P (zybrestat), AVE-8062 (ombrabulin), BNC105P, MPC-6827 (azixa), ZD6126 (ANG453), Oxi-4503, BPI-2358 (plinabulin), MN029 (denibulin), EPC-2407 (crinobulin), ZIO-301 (indibulin), T115 or BPROL075, ABT-751.
79. The combination for use according to item 77 or 78, wherein the tubulin polymerization inhibitor is plinabulin.
80. The combination for use according to any one of items 77 to 79, wherein said poly (ADP-ribose) polymerase (PARP) inhibitor is selected from olaparib, niraparib, veliparib, talazoparib, rucaparib, iniparib, fluzoparib, AZD2461, UPF 1069, PJ34, A-966492, AG-14361, E7449 and NMS-P118.
81. The combination for use according to any one of items 77 to 80, wherein said poly (ADP-ribose) polymerase (PARP) inhibitor is olaparib.
82. The combination for use according to any one of items 77 to 81, wherein said cancer is as defined in any one of items 45 to 65.

The invention claimed is:
1. A method of treating, or alleviating ovarian cancer, pancreatic cancer, or prostate cancer, comprising administering to a human in need thereof:
(i)       $N^2$-[2-(5-methoxy-1H-indol-3-yl)ethyl]-$N^4$-(1-methyl-1H-indol-4-yl)pyrimidine-2,4-diamine (NOV202), or a pharmaceutically acceptable salt, hydrate, solvate or amorphous solid thereof, wherein the amount of (i) administered to the human is a dose of in the range of 2.5-5 mg/kg, and (ii) olaparib, or a pharmaceutically acceptable salt, hydrate, solvate or amorphous solid thereof, wherein the amount of (ii) administered to the human is a dose of in the range of 400 mg/day-1200 mg/day.

2. The method of claim 1, wherein said cancer is a primary tumor.

3. The method of claim 1, wherein said cancer is a metastasis.

4. The method of claim 1, wherein said cancer is a solid tumor.

5. The method of claim 1, wherein said cancer is a BRCA mutated tumor.

6. The method of claim 1, wherein said cancer is a p53 suppressor gene mutated tumor.

7. The method of claim 1, wherein said cancer is a homologous recombination repair defect tumor with mutations in repair genes other than BRCA1/BRCA2.

8. The method of claim 1, wherein the cancer is ovarian cancer.

9. The method of claim 1, wherein the cancer is pancreatic cancer.

10. The method of claim 1, wherein the cancer is prostate cancer.

11. The method of claim 1, wherein the dose of (i) is 2.5 mg/kg.

\* \* \* \* \*